United States Patent [19]
Bolling et al.

[11] Patent Number: 5,322,769
[45] Date of Patent: *Jun. 21, 1994

[54] METHODS FOR USING CKS FUSION PROTEINS

[75] Inventors: Timothy J. Bolling, Gurnee; Wlodzimierz Mandecki, Libertyville; Sushil G. Devare, Northbrook; James M. Casey, Zion; Suresh M. Desai, Libertyville, all of Ill.

[73] Assignee: Abbott Laboratories, Abbott Park, Ill.

[*] Notice: The portion of the term of this patent subsequent to Jun. 23, 2009 has been disclaimed.

[21] Appl. No.: 903,043

[22] Filed: Jun. 23, 1992

Related U.S. Application Data

[63] Continuation-in-part of Ser. No. 276,263, Nov. 23, 1988, Pat. No. 5,124,255, which is a continuation-in-part of Ser. No. 167,067, Mar. 11, 1988, abandoned.

[51] Int. Cl.⁵ .......................................... G01N 33/543
[52] U.S. Cl. .......................................... 435/5; 435/7.1; 435/7.2; 435/7.92; 530/324; 530/327
[58] Field of Search ............... 435/5, 7.1, 7.2, 7.92; 530/324, 327

[56] References Cited

U.S. PATENT DOCUMENTS

| | | | |
|---|---|---|---|
| 4,784,941 | 11/1988 | Watanabe | 435/5 |
| 5,017,687 | 5/1991 | Vahine et al. | 530/324 |
| 5,032,511 | 7/1991 | Takahashi | 435/69.1 |
| 5,156,949 | 10/1992 | Luciw et al. | 535/5 |

OTHER PUBLICATIONS

Tijssen: Practice & Theory of Enzyme Immunoassays Elsevier 1985.

Primary Examiner—Christine M. Nucker
Assistant Examiner—Jeffrey Stucker
Attorney, Agent, or Firm—Priscilla Porembski; Andrea C. Walsh

[57] ABSTRACT

Improved methods for detecting antibodies in test samples. The improvement comprises uses CKS-fusion proteins specific for the antibodies in assays such as screening assays, competitive assays, confirmatory assays and immunodot assays. Test kits which contain these CKS-fusion proteins useful in such assays also are provided.

10 Claims, 18 Drawing Sheets

FIG. 4
SYNTHETIC PROMOTER REGION OF pTB201

```
EcoRI                                                                    PROMOTER              TRANSCRIPTION START
  |         -60    Oligo 1                          -35              -10   Oligo 3    1
AATTCCCATTAATTGAGTTAGCTCACTCATTAGGCACCCCAGGCTTTATGTTCCGGCTCGTATTTTGTGTGGAATTGTGAGCGGATAACAATTGGG
           GGGTAATTAACTCAATCGAGTGAGTAATCCGTGGGGTCCGAAATGTGAAA|TACAAGGCCGAGCATAAACACACCTTAACACTCGCCTATTGTTAACCC-
                         Oligo 2                           A                   Oligo 4

Sall               HpaII
BamHI                                                        |                 90 |
  |        30                   60
|GATCCAGTAAGGAGGTTTAAATGAGTTTGTGGTCATTATTCCCGGCGCTACGGCGTCGACGGCGTCGCC
 CTAG|GTCATTCCTCCAAATTTACTCAAACACCAGTAATAAGGGCGCGATGCCGCAGCTGCCGCAGACGGC
    RBS             METSerPheValValIleIleProAlaArgTyrAlaSerThrArgLeuPro
                                                 B                 kdsB Gene
```

| NO. | Y. POS. | AREA | MARK | % |
|---|---|---|---|---|
| 1 | 83.8 | 6.753 |  | 0.0 |
| 2 | 85.1 | 235.503 |  | 0.3 |
| 3 | 86.5 | 38.445 |  | 0.0 |
| 4 | 88.6 | 513.300 |  | 0.7 |
| 5 | 90.7 | 673.238 |  | 1.0 |
| 6 | 92.8 | 573.726 |  | 0.2 |
| 7 | 94.2 | 101.197 | V | 0.1 |
| 8 | 95.0 | 319.117 | V | 0.4 |
| 9 | 95.7 | 267.394 | V | 0.4 |
| 10 | 96.8 | 1640.438 | V | 2.5 |
| 11 | 98.2 | 1330.840 | V | 2.0 |
| 12 | 99.1 | 908.457 | V | 1.3 |
| 13 | 100.2 | 1297.070 | V | 1.9 |
| 14 | 101.4 | 353.679 | V | 0.5 |
| 15 | 103.1 | 1716.504 | V | 2.6 |
| 16 | 104.8 | 1644.469 | V | 2.5 |
| 17 | 107.4 | 49672.63 |  | 76.4 |
| 18 | 110.8 | 216.800 |  | 0.3 |
| 19 | 111.9 | 53.242 |  | 0.0 |
| 20 | 112.7 | 46.527 | V | 0.0 |
| 21 | 113.7 | 345.621 | V | 0.5 |
| 22 | 116.0 | 134.054 |  | 0.2 |
| 23 | 116.8 | 9.308 |  | 0.0 |
| 24 | 117.4 | 28.648 | V | 0.0 |
| 25 | 118.8 | 262.964 | V | 0.4 |
| 26 | 120.5 | 663.109 | V | 1.0 |
| 27 | 122.3 | 917.160 | V | 1.4 |
| 28 | 124.7 | 953.421 | V | 1.4 |
| 29 | 126.8 | 7.957 |  | 0.0 |
| 30 | 127.8 | 63.953 |  | 0.0 |
| | TOTAL | 64995.53 | | |

FIGURE 9-A

P120_SYNP41FL  Linear  LENGTH = 1199 (PART 1)

BamHI  (NarI)

1   CTCTGGATCCCCGGCGACCCGGGTGGTGGTGACATGCGTGACAACTGCGTTCTGAACTGTACAAATAC       69
    LeuTrpIleProGlyAspProGlyGlyGlyAspMETArgAspAsnTrpArgSerGluLeuTyrLysTyr
                                                                       6

INSERT 1

70  AAAGTTGTTAAAATCGAACCGCTGGGTGTTGCTCCGACTAAAGCTAAACGTCGTGTTGTTCAGCGTGAA    138
    LysValValLysIleGluProLeuGlyValAlaProThrLysAlaLysArgArgValValGlnArgGlu

139 AAACGCGCCGTTGGTATCGGTGCACTGTTCCTGGGTGCTCTGGTTCTACCATGGGTGCT             207
    LysArgAlaValGlyIleGlyAlaLeuPheLeuGlyAlaAlaAlaGlySerThrMETGlyAla

208 GCTTCTATGACCCTGACTGTTCAGGCCCGTCAGCTTCGTCTGGTATCGTTCAGCAGAACAATCTG       276
    AlaSerMETThrLeuThrValGlnAlaArgGlnLeuArgLeuValGlnGlnAsnAsnLeu

277 CTGCGTGCTATCGAAGCTCAGCAGCATCTGCTGCAACCGTTTGGGTATCAAACAGCTTCAGGCT        345
    LeuArgAlaIleGluAlaGlnGlnHisLeuLeuGlnLeuThrValTrpGlyIleLysGlnLeuGlnAla

346 CGTATCCTGGCTGTGTTGAAAGACCAGCAGCTGCTGGGTATCTGGGGTTGCTCTGGTAAA            414
    ArgIleLeuAlaValGluArgTyrLeuLysAspGlnGlnLeuLeuGlyIleTrpGlyCysSerGlyLys

415 CTGATCTGCACTACTGCTGTTCCGTGGAACGCTTCTTGGTCTAACAAATCTCTGAACAGATCTGAAC     483
    LeuIleCysThrThrAlaValProTrpAsnAlaSerTrpSerAsnLysSerLeuGluGlnIleTrpAsn

FIGURE 9-B (PART 2)

FIGURE 9-C

P120_SYNP41FL    Linear    LENGTH = 1199 (PART 3)

898  CTGTGCCTGTTCTCTTACCACCGTCGCTGCGTGATCGTGCTGACTCGTGTATCGTTGAACTGCTC  966
     LeuCysLeuPheSerTyrHisArgLeuArgAspLeuLeuIleValThrArgIleValGluLeuLeu

967  GGCCGTCGTGGTTGGGAAGCTCTGAAATACTGGTGGAATCTGCTTCAGTACTGGTCCCAGGAACTGAAA  1035
     GlyArgArgGlyTrpGluAlaLeuLysTyrTrpTrpAsnLeuLeuGlnTyrTrpSerGlnGluLeuLys

1036 AACTCTGCTGTTTCTCTGCTGAACGCTACTGCTGTTGCTGAAGGCACCGATCGTGTATCGAA  1104
     AsnSerAlaValSerLeuLeuAsnAlaThrAlaIleAlaValAlaGluGlyThrAspArgValIleGlu

1105 GTAGTTCAGGGTGCTTACCGTGCTATCCGTCACATtCCCGCTGCTTACCGTGCTATCCGTGCTTCAGGGTGCTTACCGTGCTATCCGTCACATtCCCGCGTCGTATCCGTGCTTCAGGGTCCTGGAACGTATC  1173
     ValValGlnGlyAlaTyrArgAlaIleArgHisIleProArgArgIleArgGlnGlyLeuGluArgIle

1174 CTGCTGTAAGCAGGTGGTACCTGCCG  1199
     LeuLeu
                 ────┬────
                   KpnI
             1194

SYNTHETIC HIV-2 TMP FRAGMENT SEQUENCE

```
HindIII    BglII                    27                                              54
AGC TTA AAG ATC TAC TCT TCC GCT CAC GGC CGT CAC ACC CGT GGC GTT TTC GTT
Ser Leu Lys Ile Tyr Ser Ser Ala His Gly Arg His Thr Arg Gly Val Phe Val
linker sequences ——|—— HIV-2 TMP ——

81                                             108
CTG GGC TTC CTG GGC TTC CTG GCT ACC GCG GGC TCC GCT ATG GGC GCT GCT TCC
Leu Gly Phe Leu Gly Phe Leu Ala Thr Ala Gly Ser Ala MET Gly Ala Ala Ser 135                                             162
CTG ACC GTT TCC GCT CAG TCC CGT ACC CTG CTG GCT GGC ATC GTT CAG CAG CAG
Leu Thr Val Ser Ala Gln Ser Arg Thr Leu Leu Ala Gly Ile Val Gln Gln Gln 189                                             216
CAG CAA CTT CTA GAC GTT GTT AAA CGT CAG CAG GAG CTC CTG CGT CTG ACC GTT
Gln Gln Leu Leu Asp Val Val Lys Arg Gln Gln Glu Leu Leu Arg Leu Thr Val 243                                             270
TGG GGC ACC AAA AAC CTG CAG GCT CGT GTT ACC GCT ATC GAA AAA TAC CTG CAG
Trp Gly Thr Lys Asn Leu Gln Ala Arg Val Thr Ala Ile Glu Lys Tyr Leu Gln 297                                             324
GAC CAG GCT CGT CTG AAT TCC TGG GGC TGC GCT TTC CGT CAG GTT TGC CAC ACC
Asp Gln Ala Arg Leu Asn Ser Trp Gly Cys Ala Phe Arg Gln Val Cys His Thr

NcoI    SalI
ACC GTT CCA TGG TCG A
Thr Val Pro Trp Ser
              |— linker ——
```

METHODS FOR USING CKS FUSION PROTEINS

RELATED APPLICATIONS

This application is a continuation-in-part of U.S. patent application Ser. No. 07/276,263, filed Nov. 23, 1988, now U.S. Pat. No. 5,124,255 which is a continuation-in-part of U.S. patent application Ser. No. 07/167,067, filed Mar. 11, 1988, now abandoned, which are incorporated herein by reference. This application is related to U.S. patent application Ser. No. 07/893,858, filed Jun. 5, 1992 and U.S. patent application Ser. No. 07/573,103 filed Aug. 24, 1990, which also enjoy common ownership and are incorporated herein by reference.

BACKGROUND OF THE INVENTION

This invention relates to methods for using fusion proteins produced in microbial hosts and more particularly, relates to assays utilizing CKS fusion proteins.

It is well established that prokaryotic or eukaryotic proteins can be expressed in microbial hosts where such proteins are not normally present in such hosts (i.e. are "heterologous" to the cells). Generally, such protein expression is accomplished by inserting the DNA sequence which codes for the protein of interest downstream from a control region (e.g. a lac operon) in plasmid DNA, which plasmid is inserted into the cell to "transform" the cell so it can produce (or "express") the protein of interest.

Despite this conceptually straightforward procedure, there are a number of obstacles in getting a cell to synthesize a heterologous protein and subsequently, to detect and recover the protein. The heterologous gene may not be efficiently transcribed into messenger RNA (mRNA). The mRNA may be unstable and degrade prior to translation into the protein. The ribosome binding site (RBS) present on the mRNA may only poorly initiate translation. The heterologous protein produced may be unstable in the cell or it may be toxic to the cell. If no antibodies to the protein are available or if there is no other way to assay for the protein, it may be difficult to detect the synthesized protein. Lastly, even if the protein is produced, it may be difficult to purify.

Fusion systems provide a means of solving many of the aforementioned problems. The "carrier" portion of the hybrid gene, typically found on the 5' end of the gene, provides the regulatory regions for transcription and translation as well as providing the genetic code for a peptide which facilitates detection (Shuman et al., *J. Biol. Chem.* 255:168 [1980]) and/or purification (Moks et al., *Bio/Technology* 5:379 [1987]). Frequently, potential proteolytic cleavage sites are engineered into the fusion protein to allow for the removal of the homologous peptide portion (de Geus et al., *Nucleic Acids Res.* 15:3743 [1987]; Nambiar et al., *Eur. J. Biochem.* 163:67 [1987]; Imai et al., *J. Biochem.* 100:425 [1986]).

When selecting a carrier gene for a fusion system, in addition to detectability and ease of purification, it would be extremely advantageous to start with a highly expressed gene. Expression is the result of not only efficient transcription and translation but also protein stability and benignity (the protein must not harm or inhibit the cell host). Such expression is advantageous because it can enable the production of such fusion proteins for use in assays.

It is known to use cell lysates from microorganisms such as viruses, bacteria, and the like. However, it oftentimes is difficult to produce viral lysates at such levels of purity as is required by current assays. Also, the production of viral or bacterial lysates involves exposing individuals to the microorganism in order to obtain the lysate. Commercial assays are being developed which use fusion proteins of such microorganisms instead of viral lysates as assay reagents.

In addition to their use in assays to detect the presence of infectious agents, it has been discovered that fusion proteins can be useful to detect immunosuppressive agents. For example, in pending U.S. patent application Ser. No. 07/893,858 is described the use of CKS fusion proteins in assays to detect the presence and/or amount of immunosuppressive agents such as FK-506, cyclosporin and rapamycin which are macrocyclic drugs of Streptomycete origin having in vivo and in vitro immunosuppressive properties (A. W. Thomson, *Immunol. Today* 10:6–9 [1989] and B. D. Kahan et al., *Transp.* 52:185–191 [1991]), which enjoys common ownership and is incorporated herein by reference.

SUMMARY OF THE INVENTION

The present invention provides an improvement methods using fusion proteins in assays. The fusion protein is produced by an *E. coli* enzyme, CKS (CTP:CMP-3-deoxy—manno-octulosonate cytidylyl transferase or CMP-KDO synthetase), and a heterologous protein is expressed in cells transformed with a cloning vehicle which has a DNA insert coding for CKS and the heterologous protein.

The present invention provides an improvement to an assay for anti-analyte antibody in a test sample wherein (a) at least one protein specific for the analyte attached to a solid phase is contacted with a test sample for a time and under conditions suitable for protein/antibody complexes to occur, and (b) an indicator reagent comprising a signal generating compound and a specific binding member for the analyte is contacted with said complexes for a time and for a time sufficient for a reaction to occur, and wherein the signal generated is an indication of the presence of the anti-analyte antibody in the test sample, wherein the assay comprises attaching a CKS fusion protein to the solid phase as the capture reagent. The analyte is selected from the group consisting of anti-HCV antibody, anti-HIV-1 antibody, anti-HIV-2 antibody, anti-HTLV-I antibody and anti-HTLV-II antibody.

The present invention further provides a competitive assay for detecting the presence of anti-analyte antibody immunologically reactive with a protein in a fluid test sample wherein (a) first and second aliquots of the test sample are obtained, (b) the first aliquot of said sample is contacted with a protein specific for said anti-analyte antibody attached to a solid support and (c) wherein the second aliquot is contacted with unattached protein specific for said anti-analyte and then contacted with said bound protein, wherein the improvement comprises a CKS-fusion protein specific for said anti-analyte antibody attached to the solid phase of step (b) and unattached CKS-fusion protein specific for said anti-analyte antibody in step (c). Step (b) may be incubated for about 15 minutes to 2 hours before performing step (c). Alternatively, step (b) and step (c) may be performed simultaneously.

The present invention additionally provides a test kit for use in detecting the presence of anti-analyte antibody in a test sample which test kit contains a container containing at least one protein specific for said anti-analyte antibody attached to a solid phase, and wherein the improvement comprises a container container a CKS-fusion protein specific for said anti-analyte antibody attached to a solid phase. The CKS fusion protein can be a CKS-HCV fusion protein, a CKS-HIV-1 fusion protein and/or a CKS-HIV-2 fusion protein, or a CKS-HTLV-I fusion protein and/or a CKS-HTLV-II fusion protein.

BRIEF DESCRIPTION OF THE DRAWINGS

FIG. 4 is the DNA sequence for a synthetic lacP-type promoter used in the cloning vehicles of this invention.

FIG. 14 presents the DNA and amino acid sequences of the synthetic HIV-2 TMP fragment including Hind III/Bgl II linker sequences located 5' and a Sal I linker sequence located 3' to the HIV-2 TMP fragment.

DETAILED DESCRIPTION

This invention provides for assays and test kits which utilize CKS fusion proteins. The means for producing such fusion proteins is disclosed in parent patent applications Ser. No. 07/276,263, filed Nov. 23, 1988, which is a continuation-in-part of U.S. patent application Ser. No. 07/167,067, filed Mar. 11, 1988, now abandoned, which have previously been incorporated herein by reference.

Figure 1:
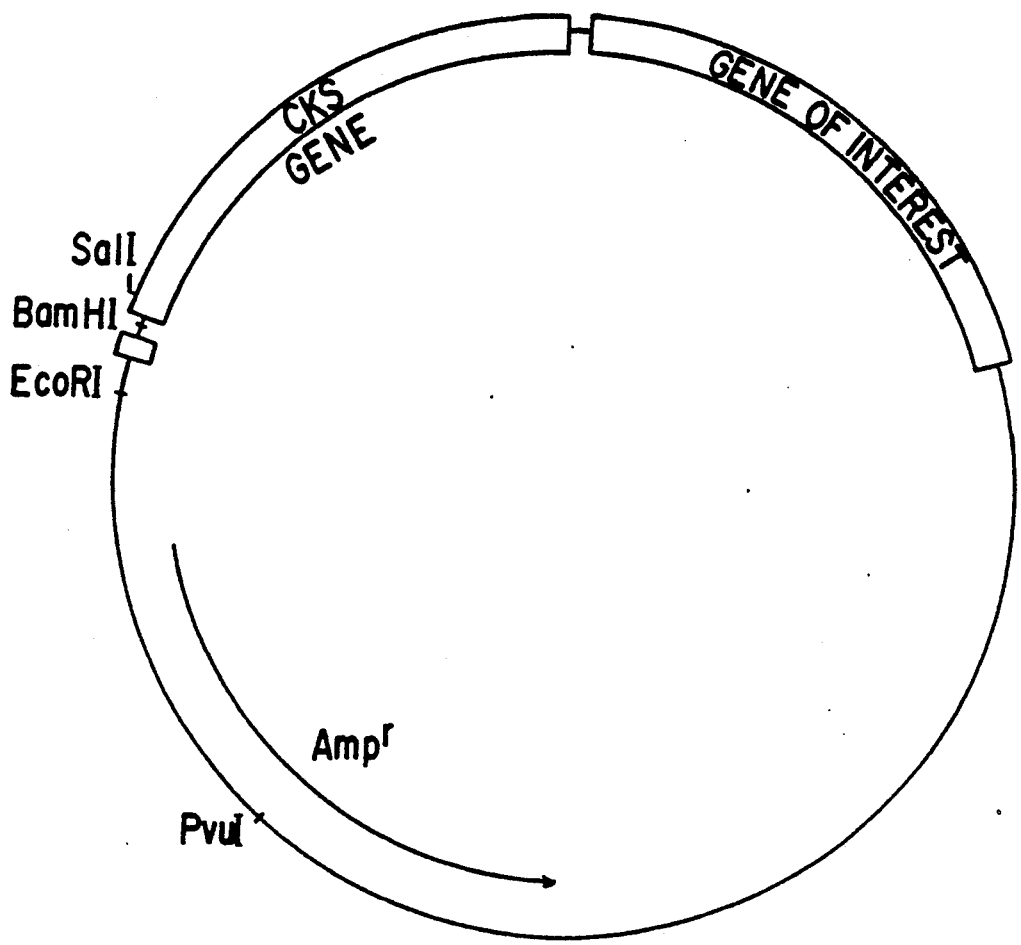
FIG. 1 is a graphic representation of a plasmid cloning vehicle.

The expression of a gene coding for a protein of interest using a DNA cloning vehicle which includes a control region, a region coding for the bacterial enzyme CKS (CMP-KDO synthetase), and a region coding for the protein of interest generally is described herein. The cloning vehicles described herein are capable of expressing fusion proteins (i.e. CKS heterologous protein fusions) at high levels. FIG. 1 shows generically the features of a plasmid useful for production of fusion proteins used in the methods of this invention. The plasmid includes a control region (e.g. a lac-type promoter with a sequence for a synthetic ribosome binding site), followed by a gene encoding CKS, which is linked to a gene coding for a heterologous protein of interest.

The use of CKS as a fusion system is novel. In addition to facilitating detection and purification of heterologous-proteins, the expression vector of this invention utilizes the kdsB gene (encoding CKS) which, with the appropriate control region, expresses at higher levels than any other gene in *E. coli* which applicants have tested. Such proteins provide reagents for assays which are safer and more cost effective than lysates produced from the native organisms.

The control region, shown in FIG. 4, includes a modified lac promoter which is essentially native lacp from −73 to +21 with two modifications: (1) a deletion at −24 of one G/C base pair, and (2) a T—A substitution at the −9 position. The control region also includes a synthetic ribosome binding site (nt 31-39) which is homologous to the 3' end of the 16S RRNA (ribosomal ribonucleic acid) in *E. coli*. Following the ribosome binding site is a consensus spacer region which is followed by the ATG translation initiation codon, followed by the structural gene for CKS.

The sequence for the structural gene encoding CKS (the kdsB gene) is published in Goldman et al., *J. Biol. Chem.* 261:15831, 1986. The amino acid sequence for CKS derived from the DNA sequence is described in the same article.

Figure 3:
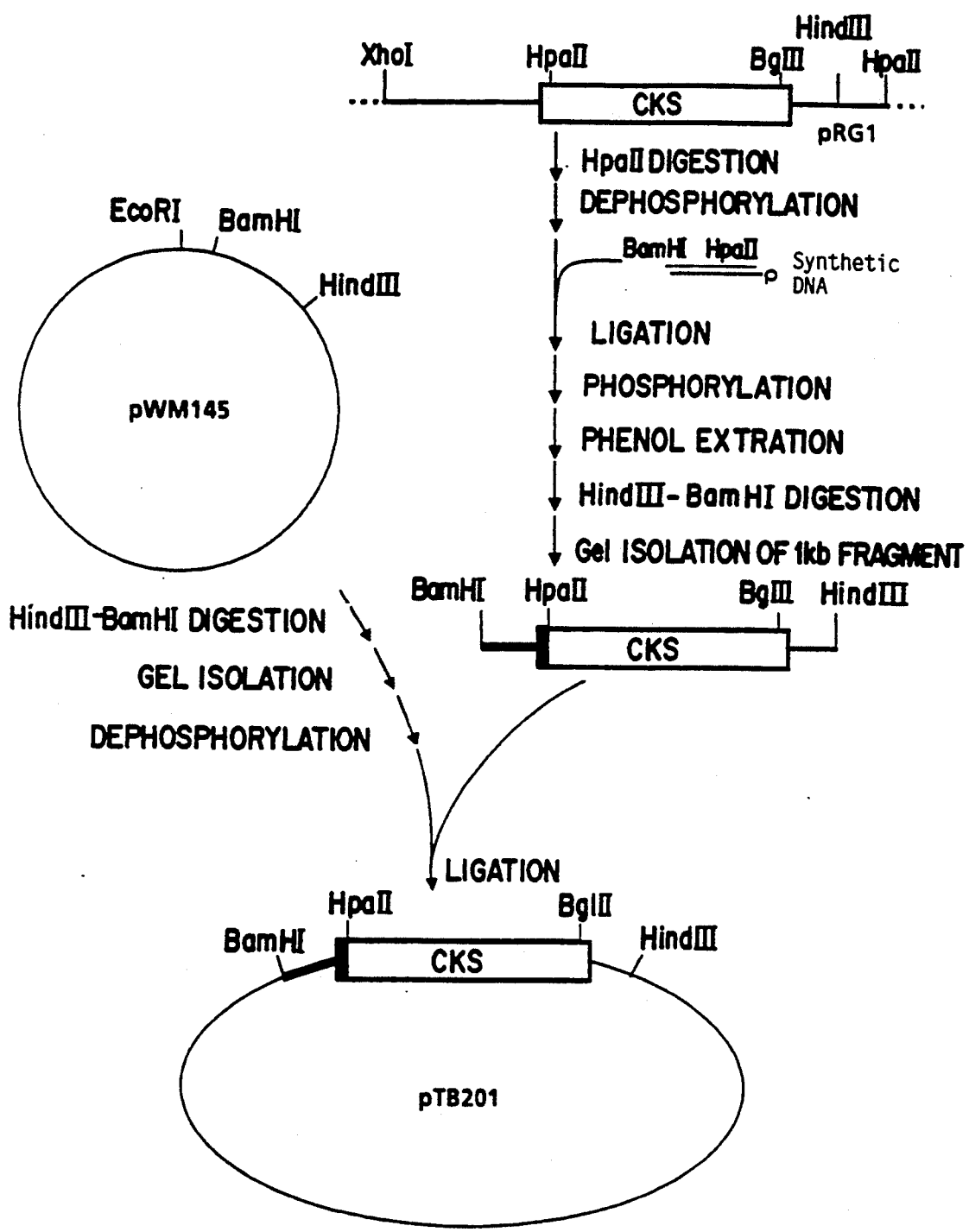
FIG. 3 is a schematic representation of the construction of pTB201 from pWM145.

The kdsB gene was obtained from Goldman's plasmid pRG1 (*J. Bacteriol.* 163:256) (FIG. 3). The first step in the kdsB gene isolation was a HpaII digestion of pRG1. Digestion with HpaII cleaved 51 base pairs from the 5' end of the gene.

A DNA fragment including the base pairs from the BamHI site to the HpaII site of FIG. 4 was constructed by annealing synthetic oligonucleotides, as described in Example 1. This DNA sequence included the ribosome binding site as well as the 51 base pairs for the 5' end of the kdsB gene. The BamHI—HpaII fragment then was ligated to the HpaII native kdsB gene containing fragment, as described in detail in Example 1. As can be seen, the ligation replaced the 51 base pairs lost to kdsB, and added the ribosome binding site for the control region.

Figure 2:
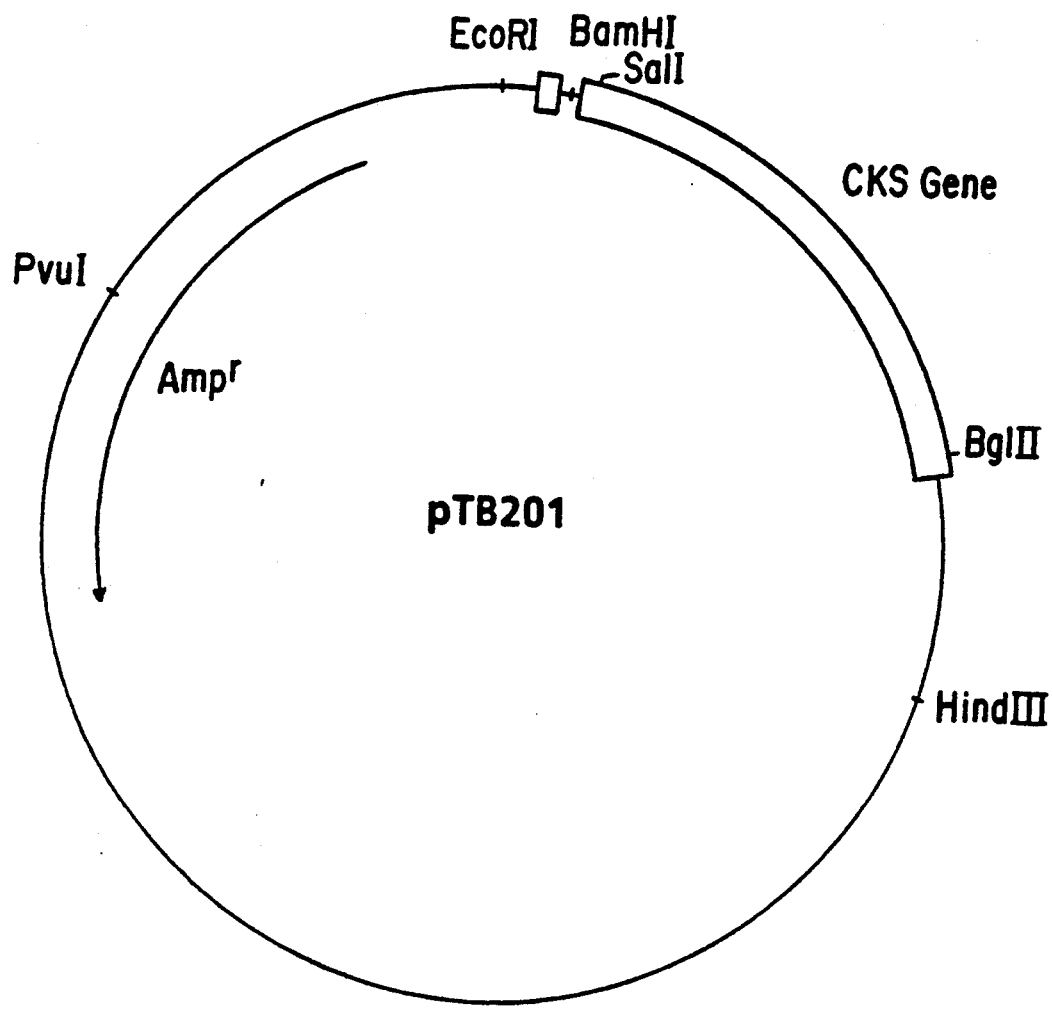
FIG. 2 is a graphic representation of a plasmid pTB201 containing a gene for CKS.
Figure 7:
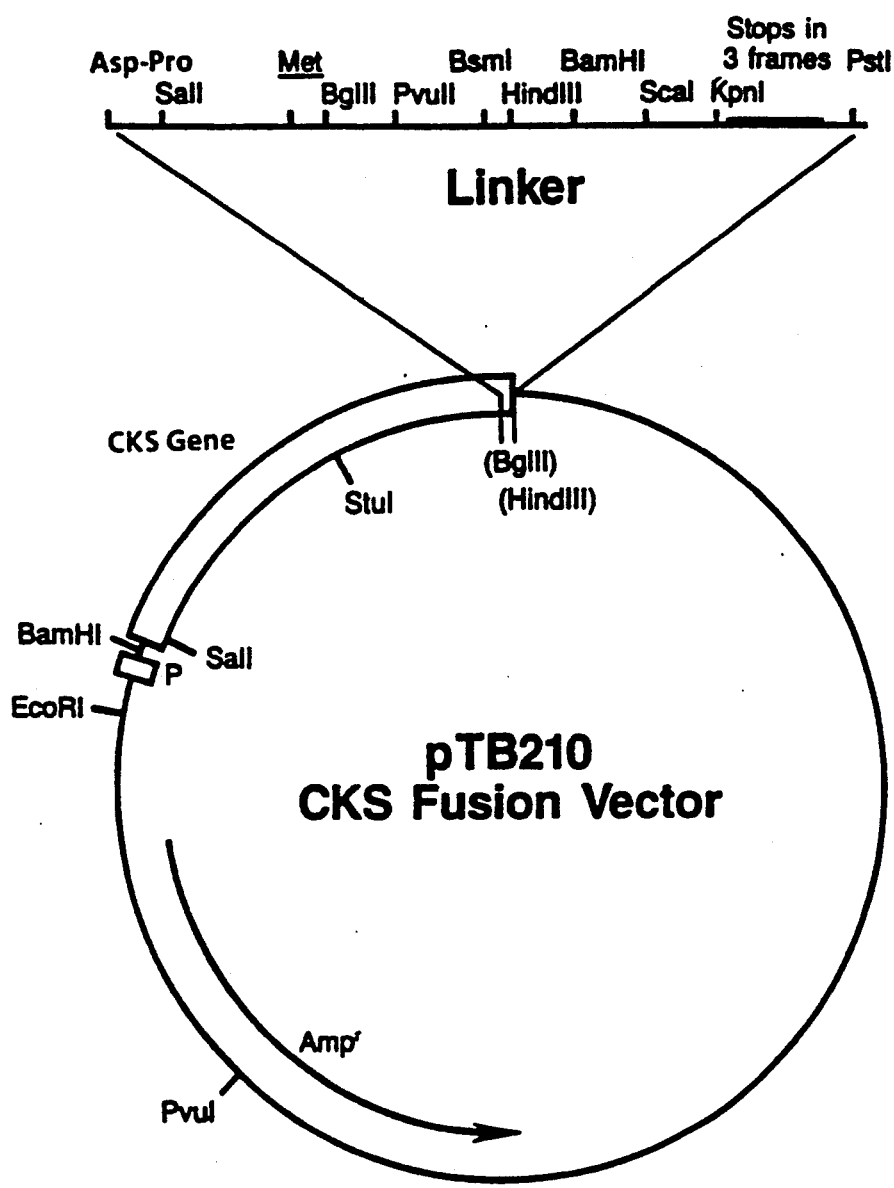
FIG. 7 is a graphic representation of a plasmid, pTB210, used to express HIV p41 fusion proteins.

The pWM145 plasmid containing the modified lac promoter located between the EcoRI and BamHI sites shown in FIG. 4A was digested with BamHI and HindIII to provide an insertion site for the BamHI—HindIII fragment containing the CKS structural gene. (FIG. 3) The kdsB containing fragment then was ligated into the pWM145 vector, assembling the control region containing the modified lac promoter and the ribosome binding site in the process. This produced plasmid pTB201 (FIGS. 2 and 3).

pTB201 is a fusion expression vector for heterologous genes which have the appropriate reading frame when cloned into the BglII or the BglII—HindIII sites (FIG. 2). However, the versatility of pTB201 can be improved by introducing other restriction endonuclease cloning sites. This is shown in FIG. 7 where a linker containing multiple restriction sites replaces the BglII-HindIII fragment of pTB201 to produce a new vector, pTB210. The linker also includes a sequence coding for Asp-Pro which allows for cleavage of the CKS protein from the heterologous protein fused to it.

The linker of FIG. 7 also includes stop codons in all three reading frames, placed downstream of the restriction sites. Thus, regardless of what heterologous structural gene or portion thereof is inserted in the linker, translation will terminate immediately after the inserted gene.

Insertion of heterologous genes into a plasmid of this invention can be accomplished with various techniques, including the techniques disclosed in U.S. patent application Ser. No. 883,242 entitled "Method for Mutagenesis By Oligonucleotide-Directed Repair of a Strand Break" filed Jul. 8, 1986, in U.S. patent application Ser. No. 131,973 entitled "FokIMethod of Gene Synthesis" filed Dec. 11, 1987, and in U.S. patent application Ser. No. 132,089 entitled "Method for Mutagenesis by Oligonucleotide-Directed Repair of a Strand Break" filed Dec. 11, 1987 which are incorporated herein by reference.

These CKS fusion proteins can be utilized in various assay formats as capture reagents or protein binders in numerous ways. After preparing the recombinant proteins as described herein, the CKS recombinant proteins can be used to develop unique assays as described herein to detect either the presence of a specific binding member of a specific binding pair. These recombinant proteins also can be used to develop monoclonal and/or polyclonal antibodies with a specific recombinant protein or synthetic peptide which specifically binds to the specific binding member of a specific binding pair.

It is contemplated that the reagent employed for the assay can be provided in the form of a kit with one or more containers such as vials or bottles, with each container containing a separate reagent such as a monoclonal antibody, or a cocktail of monoclonal antibodies, or a recombinant protein employed in the assay.

"Solid phases" ("solid supports") are known to those in the art and include the walls of wells of a reaction tray, test tubes, polystyrene beads, magnetic beads, nitrocellulose strips, membranes, microparticles such as latex particles, and others. The "solid phase" is not critical and can be selected by one skilled in the art. Thus, latex particles, microparticles, magnetic or non-magnetic beads, membranes, plastic tubes, walls of microtiter wells, glass or silicon chips and sheep red blood cells are all suitable examples. Suitable methods for immobilizing peptides on solid phases include ionic, hydrophobic, covalent interactions and the like. A "solid phase", as used herein, refers to any material which is insoluble, or can be made insoluble by a subsequent reaction. The solid phase can be chosen for its intrinsic ability to attract and immobilize the capture reagent. Alternatively, the solid phase can retain an additional receptor which has the ability to attract and immobilize the capture reagent. The additional receptor can include a charged substance that is oppositely charged with respect to the capture reagent itself or to a charged substance conjugated to the capture reagent. As yet another alternative, the receptor molecule can be any specific binding member which is immobilized upon (attached to) the solid phase and which has the ability to immobilize the capture reagent through a specific binding reaction. The receptor molecule enables the indirect binding of the capture reagent to a solid phase material before the performance of the assay or during the performance of the assay. The solid phase thus can be a plastic, derivatized plastic, magnetic or non-magnetic metal, glass or silicon surface of a test tube, microtiter well, sheet, bead, microparticle, chip, and other configurations known to those of ordinary skill in the art.

It is contemplated and within the scope of the invention that the solid phase also can comprise any suitable porous material with sufficient porosity to allow access by detection antibodies and a suitable surface affinity to bind antigens. Microporous structures are generally preferred, but materials with gel structure in the hydrated state may be used as well. Such useful solid supports include:

natural polymeric carbohydrates and their synthetically modified, cross-linked or substituted derivatives, such as agar, agarose, cross-linked alginic acid, substituted and cross-linked guar gums, cellulose esters, especially with nitric acid and carboxylic acids, mixed cellulose esters, and cellulose ethers; natural polymers containing nitrogen, such as proteins and derivatives, including cross-linked or modified gelatins; natural hydrocarbon polymers, such as latex and rubber; synthetic polymers which may be prepared with suitably porous structures, such as vinyl polymers, including polyethylene, polypropylene, polystyrene, polyvinylchloride, polyvinylacetate and its partially hydrolyzed derivatives, polyacrylamides, polymethacrylates, copolymers and terpolymers of the above polycondensates, such as polyesters, polyamides, and other polymers, such as polyurethanes or polyepoxides; porous inorganic materials such as sulfates or carbonates of alkaline earth metals and magnesium, including barium sulfate, calcium sulfate, calcium carbonate, silicates of alkali and alkaline earth metals, aluminum and magnesium; and aluminum or silicon oxides or hydrates, such as clays, alumina, talc, kaolin, zeolite, silica gel, or glass (these materials may be used as filters with the above polymeric materials); and mixtures or copolymers of the above classes, such as graft copolymers obtained by initializing polymerization of synthetic polymers on a pre-existing natural polymer. All of these materials may be used in suitable shapes, such as films, sheets, or plates, or they may be coated onto or bonded or laminated to appropriate inert carriers, such as paper, glass, plastic films, or fabrics.

The porous structure of nitrocellulose has excellent absorption and adsorption qualities for a wide variety of reagents including monoclonal antibodies. Nylon also possesses similar characteristics and also is suitable. It is contemplated that such porous solid supports described hereinabove are preferably in the form of sheets of thickness from about 0.01 to 0.5 mm, preferably about 0.1 mm. The pore size may vary within wide limits, and is preferably from about 0.025 to 15 microns, especially from about 0.15 to 15 microns. The surfaces of such supports may be activated by chemical processes which cause covalent linkage of the antigen or antibody to the support. The irreversible binding of the antigen or antibody is obtained, however, in general, by adsorption on the porous material by poorly understood hydrophobic forces. Suitable solid supports also are described in U.S. patent application Ser. No. 227,272.

The present invention provides assays which utilize specific binding members. A "specific binding member," as used herein, is a member of a specific binding pair. That is, two different molecules where one of the molecules through chemical or physical means specifically binds to the second molecule. Therefore, in addition to antigen and antibody specific binding pairs of common immunoassays, other specific binding pairs can include biotin and avidin, carbohydrates and lectins, complementary nucleotide sequences, effector and receptor molecules, cofactors and enzymes, enzyme inhibitors and enzymes, and the like. Furthermore, specific binding pairs can include members that are analogs of the original specific binding members, for example, an analyte-analog. Immunoreactive specific binding members include antigens, antigen fragments, antibodies and antibody fragments, both monoclonal and polyclonal, and complexes thereof, including those formed by recombinant DNA molecules. The term "hapten", as used herein, refers to a partial antigen or non-protein binding member which is capable of binding to an antibody, but which is not capable of eliciting antibody formation unless coupled to a carrier protein. "Analyte," as used herein, is the substance to be detected which may be present in the test sample. The analyte can be any substance for which there exists a naturally occurring specific binding member (such as, an antibody), or for which a specific binding member can be prepared. Thus, an analyte is a substance that can bind to one or more specific binding members in an assay. "Analyte" also includes any antigenic substances, haptens, antibodies, and combinations thereof. As a member of a specific binding pair, the analyte can be detected by means of naturally occurring specific binding partners (pairs) such as the use of intrinsic factor protein as a member of a specific binding pair for the determination of Vitamin B12, the use of folate-binding protein to determine folic acid, or the use of a lectin as a member of a specific binding pair for the determination of a carbohydrate. The analyte can include a protein, a peptide, an amino acid, a hormone, a steroid, a vitamin, a drug including those administered for therapeutic purposes as well as those administered for illicit purposes, a bacterium, a virus, and metabolites of or antibodies to any of the above substances. The details for the preparation of such antibodies and the suitability for use as specific binding members are well known to those skilled in the art. Viruses which can be tested include hepatitis-causing viruses (for example, hepatitis A virus, hepatitis B virus, hepatitis C virus, hepatitis delta, and hepatitis E virus), human immunodeficiency viruses (such as HIV-1, HIV-2), the HTLV-I and HTLV-II viruses, and the like.

"Indicator Reagents" may be used in the various assay formats described herein. The "indicator reagent" comprises a "signal generating compound" (label) which is capable of generating a measurable signal detectable by external means conjugated (attached) to a specific binding member for the analyte. "Specific binding member" as used herein means a member of a specific binding pair. That is, two different molecules where one of the molecules through chemical or physical means specifically binds to the second molecule. In addition to being an antibody member of a specific binding pair for the analyte, the indicator reagent also can be a member of any specific binding pair, including either hapten-anti-hapten systems such as biotin or anti-biotin, avidin or biotin, a carbohydrate or a lectin, a complementary nucleotide sequence, an effector or a receptor molecule, an enzyme cofactor and an enzyme, an enzyme inhibitor or an enzyme, and the like. An immunoreactive specific binding member can be an antibody, an antigen, or an antibody/antigen complex that is capable of binding either to the analyte as in a sandwich assay, to the capture reagent as in a competitive assay, or to the ancillary specific binding member as in an indirect assay.

The various "signal generating compounds" (labels) contemplated include chromogens, catalysts such as enzymes, luminescent compounds such as fluorescein and rhodamine, chemiluminescent compounds, radioactive elements, and direct visual labels. Examples of enzymes include alkaline phosphatase, horseradish peroxidase, beta-galactosidase, and the like. The selection of a particular label is not critical, but it will be capable of producing a signal either by itself or in conjunction with one or more additional substances.

The term "test sample" includes biological samples which can be tested by the methods of the present invention described herein and include human and animal body fluids such as whole blood, serum, plasma, cerebrospinal fluid, urine, lymph fluids, and various external secretions of the respiratory, intestinal and genitourinary tracts, tears, saliva, milk, white blood cells, myelomas and the like, biological fluids such as cell culture supernatants, fixed tissue specimens and fixed cell specimens. Any substance which can be adapted for testing with the CKS recombinant proteins and assay formats of the present invention are contemplated to be within the scope of the present invention.

Other embodiments which utilize various other solid phases also are contemplated and are within the scope of this invention. For example, ion capture procedures for immobilizing an immobilizable reaction complex with a negatively charged polymer, described in co-pending U.S. patent application Ser. No. 150,278 corresponding to EP publication 0326100, and U.S. patent application Ser. No. 375,029 (EP publication no. 0406473) both of which enjoy common ownership and are incorporated herein by reference, can be employed according to the present invention to effect a fast solution-phase immunochemical reaction. An immobilizable immune complex is separated from the rest of the reaction mixture by ionic interactions between the negatively charged poly-anion/immune complex and the previously treated, positively charged porous matrix and detected by using various signal generating systems previously described, including those described in chemiluminescent signal measurements as described in co-pending U.S. patent application Ser. No. 921,979 corresponding to EPO Publication No. 0 273,115, which enjoys common ownership and which is incorporated herein by reference.

Also, the methods of the present invention can be adapted for use in systems which utilize microparticle technology including an automated and semi-automated systems wherein the solid phase comprises a microparticle. Such systems include those described in pending U.S. patent applications Ser. No. 425,651 and 425,643, which correspond to published EPO applications Nos. EP 0 425 633 and EP 0 424 634, respectively, which are incorporated herein by reference.

The use of scanning probe microscopy (SPM) for immunoassays also is a technology to which the recombinant proteins of the present invention or monoclonal antibodies produced from these recombinant proteins are easily adaptable. In scanning probe microscopy, in particular in atomic force microscopy, the capture phase, for example, either a CKS recombinant protein or a monoclonal antibody produced therefrom, is adhered to a solid phase, the test sample is contacted to the solid phase for a time and under conditions sufficient for a reaction between the two to occur, and a scanning probe microscope is utilized to detect antigen/antibody complexes which may be present on the surface of the solid phase. The use of scanning tunnelling microscopy eliminates the need for labels which normally must be utilized in many immunoassay systems to detect antigen/antibody complexes. Such a system is described in pending U.S. patent application Ser. No. 662,147, which enjoys common ownership and is incorporated herein by reference.

The use of SPM to monitor specific binding reactions can occur in many ways. In one embodiment, one member of a specific binding partner (analyte specific substance which is the monoclonal antibody of the invention) is attached to a surface suitable for scanning. The attachment of the analyte specific substance may be by adsorption to a test piece which comprises a solid phase of a plastic or metal surface, following methods known to those of ordinary skill in the art. Or, covalent attachment of a specific binding partner (analyte specific substance) to a test piece which test piece comprises a solid phase of derivatized plastic, metal, silicon, or glass may be utilized. Covalent attachment methods are known to those skilled in the art and include a variety of means to irreversibly link specific binding partners to the test piece. If the test piece is silicon or glass, the surface must be activated prior to attaching the specific binding partner. Activated silane compounds such as triethoxy amino propyl silane (available from Sigma Chemical Co., St. Louis, Mo.), triethoxy vinyl silane (Aldrich Chemical Co., Milwaukee, Wis.), and (3-mercaptopropyl)-trimethoxy silane (Sigma Chemical Co., St. Louis, Mo.) can be used to introduce reactive groups such as amino-, vinyl, and thiol, respectively. Such activated surfaces can be used to link the binding partner directly (in the cases of amino or thiol) or the activated surface can be further reacted with linkers such as glutaraldehyde, bis (succinimidyl) suberate, SPPD 9 succinimidyl 3-[2-pyridyldithio]propionate), SMCC (succinimidyl-4-[N-maleimidomethyl]cyclohexane-1-carboxylate), SIAB (succinimidyl [4-iodoacetyl-]aminobenzoate), and SMPB (succinimidyl 4-[1-maleimidophenyl]butyrate) to separate the binding partner from the surface. The vinyl group can be oxidized to provide a means for covalent attachment. It also can be used as an anchor for the polymerization of various polymers such as poly acrylic acid, which can provide multiple attachment points for specific binding partners. The amino surface can be reacted with oxidized dextrans of various molecular weights to provide hydrophilic linkers of different size and capacity. Examples of oxidizable dextrans include Dextran T-40 (molecular weight 40,000 daltons), Dextran T-110 (molecular weight 110,000 daltons), Dextran T-500 (molecular weight 500,000 daltons), Dextran T-2M (molecular weight 2,000,000 daltons) (all of which are available from Pharmacia), or Ficoll (molecular weight 70,000 daltons (available from Sigma Chemical Co., St. Louis, Mo.). Also, polyelectrolyte interactions may be used to immobilize a specific binding partner on a surface of a test piece by using techniques and chemistries described by pending U.S. patent application Ser. No. 150,278, filed Jan. 29, 1988, and Ser. No. 375,029, filed Jul. 7, 1989, each of which enjoys common ownership and each of which is incorporated herein by reference. The preferred method of attachment is by covalent means. Following attachment of a specific binding member, the surface may be further treated with materials such as serum, proteins, or other blocking agents to minimize non-specific binding. The surface also may be scanned either at the site of manufacture or point of use to verify its suitability for assay purposes. The scanning process is not anticipated to alter the specific binding properties of the test piece.

In an assay format to detect the presence of antibody against a specific analyte (for example, an infectious agent such as a virus) in a human test sample, the human test sample is contacted and incubated with a solid phase coated with at least one recombinant protein (polypeptide). If antibodies are present in the test sample, they will form a complex with the antigenic polypeptide and become affixed to the solid phase. After the complex has formed, unbound materials and reagents are removed by washing the solid phase. The complex is reacted with an indicator reagent and allowed to incubate for a time and under conditions for second complexes to form. The presence of antibody in the test sample to the CKS recombinant polypeptide(s) is determined by detecting the signal generated. Signal generated above a cut-off value is indicative of antibody to the analyte present in the test sample. With many indicator reagents, such as enzymes, the amount of antibody present is proportional to the signal generated. Depending upon the type of test sample, it may be diluted with a suitable buffer reagent, concentrated, or contacted with the solid phase without any manipulation ("neat"). For example, it usually is preferred to test serum or plasma samples which previously have been diluted, or concentrate specimens such as urine, in order to determine the presence and/or amount of antibody present.

In addition, more than one recombinant protein can be used in the assay format just described to test for the presence of antibody against a specific infectious agent by utilizing CKS fusion proteins against various antigenic epitopes of the viral genome of the infectious agent under study. Thus, it may be preferred to use recombinant polypeptides which contain epitopes within a specific viral antigenic region as well as epitopes from other antigenic regions from the viral genome to provide assays which have increased sensitivity any perhaps greater specificity than using a polypeptide from one epitope. Such an assay can be utilized as a confirmatory assay. In this particular assay format, a known amount of test sample is contacted with (a) known amount(s) of at least one solid support coated with at least one recombinant protein for a time and under conditions sufficient to form recombinant protein/antibody complexes. The complexes are contacted with known amount(s) of appropriate indicator reagent(s)s for a time and under suitable conditions for a reaction to occur, wherein the resultant signal generated is compared to a negative test sample in order to determine the presence of antibody to the analyte in the test sample. It further is contemplated that, when using certain solid phases such as microparticles, each recombinant protein utilized in the assay can be attached to a separate microparticle, and a mixture of these microparticles made by combining the various coated microparticles, which can be optimized for each assay.

Variations to the above-described assay formats include the incorporation of CKS-recombinant proteins of different analytes attached to the same or to different solid phases for the detection of the presence of antibody to either analyte (for example, CKS-recombinant proteins specific for certain antigenic regions of HIV-1 coated on the same or different solid phase with CKS-recombinant proteins specific for certain antigenic region(s) of HIV-2, to detect the presence of either (or both) HIV-1 or HIV-2).

In yet another assay format, CKS recombinant proteins containing antigenic epitopes are useful in competitive assays such as neutralization assays. To perform a neutralization assay, a recombinant polypeptide representing epitopes of an antigenic region of an infectious agent such as a virus, is solubilized and mixed with a sample diluent to a final concentration of between 0.5 to 50.0 μg/ml. A known amount of test sample (preferably 10 μl), either diluted or non-diluted, is added to a reaction well, followed by 400 μl of the sample diluent containing the recombinant polypeptide. If desired, the mixture may be preincubated for approximately 15 minutes to two hours. A solid phase coated with the CKS recombinant protein described herein then is added to the reaction well, and incubated for one hour at approximately 40° C. After washing, a known amount of an indicator reagent, for example 200 μl of a peroxide labelled goat anti-human IgG in a conjugate diluent is added and incubated for one hour at 40° C. After washing and when using an enzyme conjugate such as described, an enzyme substrate, for example, OPD substrate, is added and incubated at room temperature for thirty minutes. The reaction is terminated by adding a stopping reagent such as 1N sulfuric acid to the reaction well. Absorbance is read at 492 nm. Test samples which contain antibody to the specific polypeptide generate a reduced signal caused by the competitive binding of the peptides to these antibodies in solution. The percentage of competitive binding may be calculated by comparing absorbance value of the sample in the presence of recombinant polypeptide to the absorbance value of the sample assayed in the absence of a recombinant polypeptide at the same dilution. Thus, the difference in the signals generated between the sample in the absence of recombinant protein and the sample in the absence of recombinant protein is the measurement used to determine the presence or absence of antibody.

In another assay format, the recombinant proteins can be used in immunodot blot assay systems. The immunodot blot assay system uses a panel of purified recombinant polypeptides placed in an array on a nitrocellulose solid support. The prepared solid support is contacted with a sample and captures specific antibodies (specific binding member) to the recombinant protein (other specific binding member) to form specific binding member pairs. The captured antibodies are detected by reaction with an indicator reagent. Preferably, the conjugate specific reaction is quantified using a reflectance optics assembly within an instrument which has been described in U.S. patent application Ser. No. 07/227,408 filed Aug. 2, 1988. The related U.S. patent application Ser. No. 07/227,586 and 07/227,590 (both of which were filed on Aug. 2, 1988) further described specific methods and apparatus useful to perform an immunodot assay, as well as U.S. Pat. No. 5,075,077 (U.S. Ser. No. 07/227,272 filed Aug. 2, 1988). Briefly, a nitrocellulose-base test cartridge is treated with multiple antigenic polypeptides. Each polypeptide is contained within a specific reaction zone on the test cartridge. After all the antigenic polypeptides have been placed on the nitrocellulose, excess binding sites on the nitrocellulose are blocked. The test cartridge then is contacted with a test sample such that each antigenic polypeptide in each reaction zone will react if the test sample contains the appropriate antibody. After reaction, the test cartridge is washed and any antigen-antibody reactions are identified using suitable well-known reagents. As described in the patents and patent applications listed herein, the entire process is amenable to automation. The specifications of these applications related to the method and apparatus for performing an immunodot blot assay are incorporated herein by reference.

It also is within the scope of the present invention that CKS fusion proteins can be used in assays which employ a first and second solid support, as follow, for detecting antibody to a specific antigen of an analyte in a test sample. In this assay format, a first aliquot of a test sample is contacted with a first solid support coated with CKS recombinant protein specific for an analyte for a time and under conditions sufficient to form recombinant protein/analyte antibody complexes. Then, the complexes are contacted with an indicator reagent specific for the recombinant antigen. The indicator reagent is detected to determine the presence of antibody to the recombinant protein in the test sample. Following this, the presence of a different antigenic determinant of the same analyte is determined by contacting a second aliquot of a test sample with a second solid support coated with CKS recombinant protein specific for the second antibody for a time and under conditions sufficient to form recombinant protein/second antibody complexes. The complexes are contacted with a second indicator reagent specific for the antibody of the complex. The signal is detected in order to determine the presence of antibody in the test sample, wherein the presence of antibody to either analyte recombinant protein, or both, indicates the presence of anti-analyte in the test sample. It also is contemplated that the solid supports can be tested simultaneously.

The use of haptens is known in the art. It is contemplated that haptens also can be used in assays employing CKS fusion proteins in order to enhance performance of the assay. The following examples are meant to illustrate, but not to limit, the spirit and scope of the invention.

EXAMPLES

The Examples below illustrate the concepts explained above. Example 1 describes the construction of a plasmid pTB201 which contains a modified lac promoter and the kdsB gene. In Example 2, cells containing pTB201 are used to express the CKS protein to establish that the kdsB gene is functional. In Example 3, goat anti-CKS sera is raised to detect the fusion proteins such as the one produced in Example 4. In Example 4, a fusion protein of CKS and HIV-1 p41 is disclosed. In Example 5, fusion proteins of CKS and various permutations of synthetic HIV-1 p41 and p12O are disclosed. In Example 6, a fusion protein of CKS and HSV-II gG2 is disclosed. In Example 7, a fusion protein of CKS and the "kringle" region of tPA (tissue-plasminogen-activator) is prepared. In Example 8, two fusion proteins of CKS and SPL(pVal) are prepared. In Example 9, a fusion for CKS and SPL(phe) is prepared. In Example 10, a fusion for CKS and HIV-2 is prepared. Example 11 presents the use of CKS fusion proteins in screening assay. Example 12 illustrates the use of the CKS fusion proteins of the invention in competitive assays, while Example 13 illustrates the use of CKS fusion proteins in immunoblot assays.

EXAMPLE 1

CKS Expression Vector

A. Construction and Preparation of DWM145

The plasmid, pWM145, is a derivative of the C5a expression vector, pWMlll. (Mandecki et al, *Gene* 43:131, 1986). Whereas the pWMlll vector contains a lacP-UV5-D24 promoter, the pWM145 vector contains a lacP-T9-D24 promoter. The changes were accomplished by replacing the promoter/operator region of pWMlll contained within an EcoRI-BamHI fragment with asynthetic fragment (FIG. 4A) containing the modifications. The following procedure was used.

Plasmid DNA (pWMlll) was isolated from JM83 (ara, (lac-proAB), rpsl, o8O, lacz M15) cells using a standard alkaline extraction protocol followed by purification on a cesium chloride gradient and precipitated with three volumes of 70% ethanol at −20° C. for two hours followed by centrifugation. DNA was resuspended in distilled water to a concentration of 1 mg/ml.

One microgram of pWMlll DNA was digested for two hours concomitantly with ten units of EcoRI and ten units of Bam.HI in 20 ul of a buffer consisting of 50 mm Tris, pH7.5; 10 mM $MgCl_2$; and 100 mM NaCl. Following digestion, the three kilobase plasmid was purified by 5% (50:1 acrylamide:BIS) polyacrylamide gel electrophoresis (PAGE). The fragment was cut out and extracted by shaking overnight at 37° C. in 10 volumes of 500 mM ammonium acetate, 10 mM magnesium, acetate, 1 mM EDTA, and 0.1% SDS. The DNA was precipitated by chilling it for two hours at −20° C. with 2.5 volumes of 100% ethanol, followed by centrifugation.

The EcoRI-BamHI promoter fragment was composed of four oligonucleotides (oligos 1 through 4 indicated by brackets in FIG. 4A) which were purified by 20% PAGE under denaturing conditions and annealed by mixing equal molar amount of the oligonucleotides together in ligation buffer (66 mM Tris, pH7.6; 6.6 mM $MgCl_2$; 50 μg/ml BSA; 10 MM dithiothreitol; 1 mm ATP), maintaining the mixture at 80° C. for five minutes, cooling the mixture slowly to 25° C., then refrigerating for one hour. A ten-fold molar excess of annealed oligonucleotides was ligated together with approximately 50 ng of the purified EcoRI-BamHI digested vector and one unit T4 ligase in 20 ul volume ligase buffer at 16° C. overnight. One-fourth of the ligation mix was used to transform competent JM103 (supE, thi, (lac-proAB), enda, rpsl, sbcB15, [F', traD36, proAB, laciq Z M15]) using standard protocol (Mandel and Higa, *J. Mol. Biol.* 53:154,1970). Plasmid DNA from the transformants was prepared from 150 ml cultures as described above, and the DNA was sequenced using well-known Sanger methodology (*Proc. Natl. Acad. Sci. USA* 24:5463,1977).

B. Construction and Preparation of pTB201

The kdsB gene from *E. coli* K-12, which encodes CTP:CMP-3-deoxy-manno octulosonate cytidylyltransferase (CMP-KDO synthetase), was isolated from pRG1. The gene is almost entirely contained within a HpII fragment (FIG. 3). A linker was constructed to facilitate cloning kdsB into pWM145. The linker not only provided a BamHI site for subsequent cloning but also included a strong ribosome binding site and the DNA sequence coding for 17 amino acids at the amino terminus of CKS (FIG. 4B). The procedure for construction, shown in FIG. 3, was as follows:

1(a). Plasmid pRG1 was digested with HpaII and dephosphorylated with bacterial alkaline phosphatase (BRL). The 1.7 kb kdsB gene fragment was isolated on a 5% (50:1) Acrylamide:BIS gel, eluted, and purified as described above.

1(b). Oligonucleotides (shown in FIG. 4B) were synthesized, purified, labeled (using BRL T4 Kinase, with a 2×molar excess of ATP (1 part gamma [$^{32}$P]ATP to 9 parts nonradioactive ATP) and BRL recommended protocol) and annealed.

2. Ligation of the HpaII gene fragment with the synthetic fragment was carried out at 16° C. overnight. Ligase was heat inactivated (15 min at 65° C.). DNA was then phosphorylated (as above), phenol extracted (1×1 vol buffer equilibrated phenol, 1×1 vol chloroform:isoamyl alcohol), ethanol precipitated, and resuspended in medium salt buffer (50 mM Tris, pH 7.5, 10 nMM, $Cl_2$ and 50 mM NaCl). Following simultaneous digestion with HindIII and BamHI, the DNA was purified from a 5% (50:1) acrylamide gel.

3. The pWM145 vector was digested with HindIII and Bam.HI, dephosphorylated, and purified from a 5% (50:1) acrylamide gel as above. The vector (15 ng) and insert (20 ng) were ligated overnight at 16° C. One half of the total ligation mix was used to transform competent JM103 cells. The pTB201 construct was verified by DNA sequencing.

EXAMPLE 2

Expression of kdsB Gene and Purification of CKS From pTB201/JM103 Cells

A. Cultivation of pTB201/JM103 cells

Figure 5:
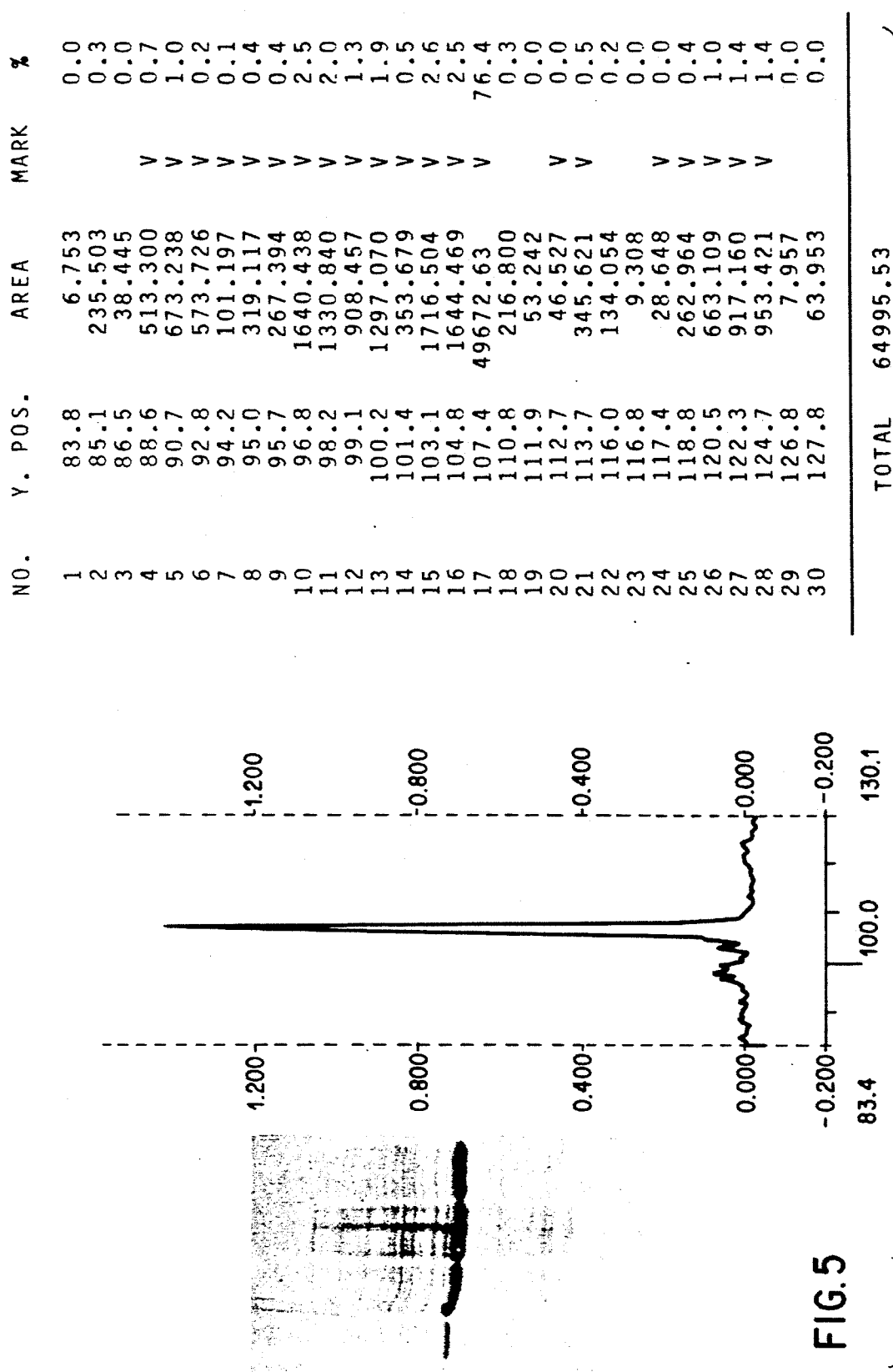
FIG. 5 is a coomassie brilliant blue-stained gel of various amounts of whole cell lysate from pTB201-containing JM103 cells. A corresponding gel scan/integration is also shown.

A 50 ml flask containing 10 ml LB broth with 50 μg/ml ampicillin was inoculated with a loopful of frozen stock pTB201/JM103 cells. The culture was incubated at 37° C. while shaking at 225 RPM. When the culture became turbid, the 10 ml were used to inoculate one liter of LB/Amp in a four liter flask. At an $OD_{600}=0.3$, IPTG (isopropyl-thio-B-galactoside) was added to a final concentration of 1 mM, and the cells were incubated overnight. A typical SDS-PAGE of the whole cell lysate as well as a gel scan on the sample is shown in FIG. 5. The relative percentage of the CKS to the total cellular proteins is 50 to 75%.

B. Purification of CKS

Purification procedure was that described by Goldman and Kohlbrenner (*J. Bacteriol.* 163:256-261) with some modifications. Cells were pelleted by centrifugation, resuspended in 50 mM potassium phosphate (pH 7.6), and lysed by two passages through a French Press (15,000 PSI). The lysate was spun at 30,000×g for 30 minutes. The soluble fraction was treated with protamine sulfate and ammonium sulfate, and dialyzed as described (Ray et al, *Methods Enzymol.* 83:535 [1982]). The sample was passed for final purification through a BioRad DEAE-5 PW HPLC-ion exchange column and eluted with a 50–400 mM potassium phosphate (10% acetylnitrile) gradient.

EXAMPLE 3

Generation of Goat Anti-CKS Sera

A. Goat immunization and bleeding

A goat was immunized monthly in three general areas—inguinal (subcutaneously), auxillary (subcutaneously) and hind leg muscles. Initial inoculation consisted of 1 mg purified CKS in complete Freund's Adjuvant. Thereafter, the boosting inoculum consisted of 0.5 mg purified CKS in incomplete Freund's Adjuvant. Five-hundred milliliters of blood was collected from the goat two and three weeks post-inoculation starting after the second boost. The blood was allowed to clot overnight, and the serum was decanted and spun at 2500 RPM for thirty minutes to remove residual red blood cells.

B. Immunoblotting

Figure 6:
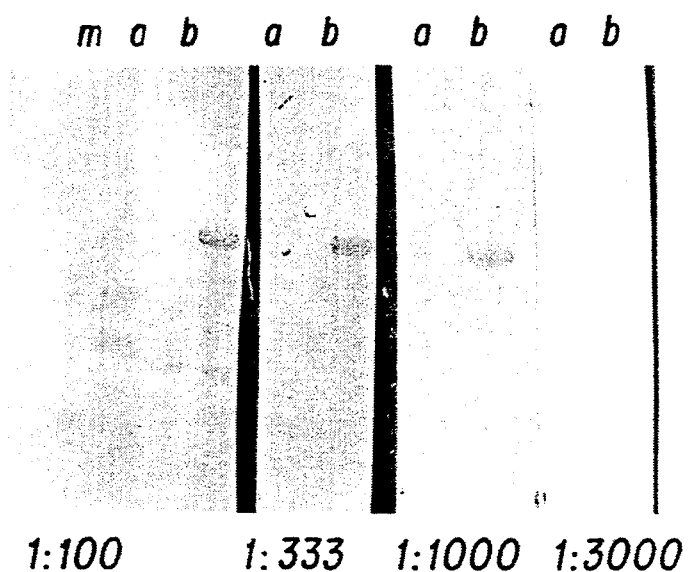
FIG. 6 shows immunoblots of CKS-producing and nonproducing cells used to optimize the titration of goat anti-CKS serum for identifying CKS fusion proteins. M is protein molecular weight markers; A, negative control JM103 whole cell lysate; B, positive control pTB201/JM103 whole cell lysate.

The presence of anti-CKS antibodies in the goat serum was confirmed by immunoblotting (FIG. 6). Whole cell lysates of pTB201/JM103 (labeled "b" in FIG. 6) and JM103 (labeled "a") controls were run on a 12.5% SDS-polyacrylamide gel, and proteins were electrophoretically transferred (Towbin, et al, *Proc. Natl. Acad. Sci. USA* 76:4350) to nitrocellulose. The filter was cut into strips which were pre-blocked with immunoblot buffer (5% instant dry milk, 1×TBS [50 mM Tris, pH 8.1; 150 mM NaCl], 0.01% Antifoam C Emulsion) for 15 minutes with agitation. Strips were placed into separate containers with immunoblot buffer and various amounts of serum (from 1:100 to 1:3000) were added. After one and one-half hours of agitation, the buffer was poured off, and the strips were washed three times for five minutes with 1×TBS. The second antibody, horseradish peroxidase-labeled rabbit anti-goat (BioRad), was added to the strips at a 1:1500 dilution in immunoblot buffer. Following one and one-half hours of agitation, the buffer was poured off, and the strips were washed as above. Blots were developed for 5 to 10 minutes with agitation after addition of the developing agent (0.5 mg/ml of 3,3'-diaminobenzidine tetrahydrochloride dehydrate, 0.1 μg/ml of $H_2O_2$ in 1×TBS). A 1:3000 dilution of the serum was optimal, giving strong positive bands and negligible background.

EXAMPLE 4

Fusion protein—CKS/HIV-1-041 HaeIII-HindIII

As an example of expression of a hybrid gene, a portion of the HIV-1 (human immunodeficiency virus type 1) p41 (envelope) gene was cloned into the CKS expression vector. The resulting gene coded for a protein fusion which consisted of CKS (less nine residues at the carboxy terminus), a nine amino acid residue linker, and a major epitope of the HIV-1 virus (amino acid positions 548–646 based on the precursor envelope protein, p160, numbering by Ratner, et al, *Nature* 313:227, 1985) (refer to FIG. 8). In order to assure the proper reading frame of the HIV-1 portion of the gene, a linker was designed and cloned into the pTB201 plasmid. The linker and HIV-1 gene fragments were cloned as close to the distal end of the kdsB gene as conveniently possible. Our rationale was that maximizing the amount of kdsB gene would maximize the chance of success for high level expression of the heterologous gene.

A. Construction of pTB210

The pTB210 plasmid (FIG. 7) was a derivative of the pTB201 plasmid (described above). pTB201 was digested with BqlII and HindIII, and the 3.6 kb vector fragment was purified from a 5% (50:1) acrylamide gel. The linker, composed of two synthetic oligonucleotides with overhangs compatible with BglII and HindIII ends, was ligated into the vector, and the ligation mixture was used to transform competent JM109 cells (recA1, endA96, thi, hsdR17, supE44, relA1,-, (lac-,proAB), [F', traD36, proAB, lacIqZ M15]). DNA sequencing was used to confirm the construction.

B. Construction of pTB211

The pTB211 plasmid was the vector construction used to express the hybrid kdsB-HIV-1 p41 major epitope gene. The source of HIV-1 DNA was a plasmid which contained the p160 gene of HIV-1 (HTLV-IIIB isolate from NIH) cloned as a KpnI fragment into pUC18. The plasmid was digested with HaeIII and HindIII and a 296 bp fragment was isolated from a 5% acrylamide gel. This fragment was ligated into PvuII-HindIII digested pTB210 vector followed by transformation into competent JM109 cells.

C. Screening of Transformants

The transformed cells were plated on LB/AMP plates. Following overnight incubation at 37° C., several colonies were picked from the plate and used to inoculate 2 ml of LB/Amp broth. Cultures were grown to an $OD_{600}$ of 0.3–0.5; then IPTG was added to a final concentration of 1 mM. Cultures were shaken at 37° C. for an additional three hours. The absorbance of the cultures at 600 nm was measured; cells from one milliliter of each culture were precipitated by centrifugation, and then resuspended to an $OD_{600}$ equivalent of ten in treatment buffer (63 MM Tris, pH 6.8, 2% SDS, 10% glycerol, 5% 2-mercaptoethanol). Following a 10 minute incubation in a boiling waterbath, an aliquot (10 ul) of each lysed culture was electrophoresed on 12.5% SDS-polyacrylamide gels. A protein band corresponding to the proper molecular weight of the fusion protein could be visualized directly on gels stained with Comassie brilliant blue. Fusion protein could also be detected by immunoblots using the goat anti-CKS serum (method described in Example 3B.) and HIV-1 positive human serum (using human serum at 1:250 dilution and HRP conjugated goat anti-human antibodies at 1:1500). The fusion protein level in the cells after induction was 5–10% of the total cellular protein.

EXAMPLE 5

Fusion protein-CKS/synthetic HIV-1 envelope peptides

In this example, hybrids of the kdsB and portions of a synthetic p41 genes expressed and produced fusion proteins to a level of up to 20% of the total cellular protein. Additionally, this example demonstrates the use of an Asp-Pro dipeptide in the linker region as a chemical cleavage site for cleaving the CKS portion of the protein from the HIV-1 portion. Further examples are included which demonstrate that multiple fusions (CKS peptide plus p41 and a portion of p12O) were attainable. These are useful peptides for diagnostics, especially in the assay formats described herein.

A. Synthesis and cloning of the HIV-1 synp41d gene

Figure 8:
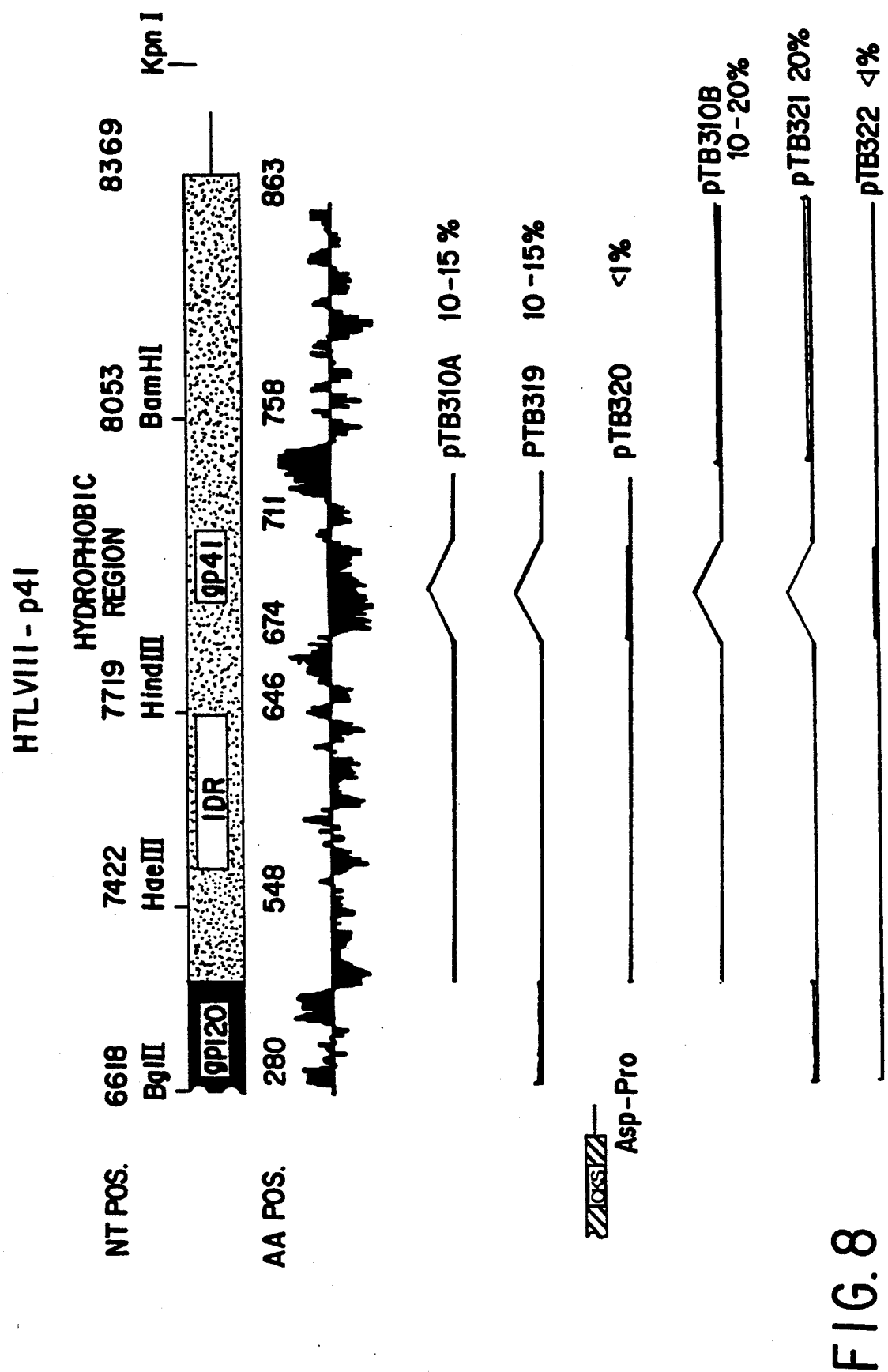
FIG. 8 shows a representation of the various synthetic p41 genes relative to the native gene. A hydrophobicity plot of the protein is also indicated. Levels of expression of each clone are included.

The synp41d gene codes for a deletion mutant of the HIV-1 p41 protein which contains a 38aa hydrophobic region deletion (from Ala674 to Val711 based on p16O numbering, refer to FIG. 8 plasmid, pTB310B). The gene was synthesized using the method of oligonucleotide directed double-stranded break repair disclosed in U.S. patent application Ser. No. 883,242 filed Jul. 8, 1986, in U.S. patent application Ser. No. 131,973 filed Dec. 11, 1987, and in U.S. patent application Ser. No. 132,089 filed Dec. 11, 1987 which are incorporated herein by reference. The specific sequence is indicated by single-line overscore on FIG. 9. The synthetic gene contained flanking BamHI and KpnI sites to facilitate cloning into PTB210. The vector was digested with BqlII and KpnI, and the BamHI-KpnI synthetic gene fragment was ligated into the vector. Following transformation into JM109 cells, clones were cultivated, induced, and screened for expression.

B. Characterization of fusion protein encoded by pTB310A

Figure 9:
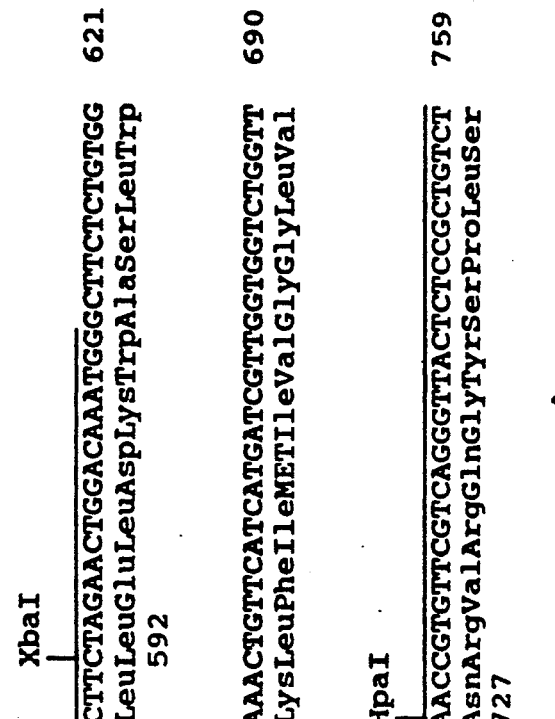
FIGS. 9-A, 9-B, and 9-C is a sequence of the synthetic p41 full-length gene with the carboxy terminus of pl20. The broken line over the sequence indicates the sequence of pTB310B. The sequence of pTB310A is the same as pTB310B except for the deletion of an A (nt 813) indicated by the . Plasmid pTB321 includes Insert 1 (nt 15-143) which encode the carboxy terminus of pl20. Plasmid pTB322 contains Insert 2 (nt 610-720) which encodes the hydrophobic region of p41.

Upon the initial screening, a clone was discovered containing a plasmid (pTB310A) which had a A/T base deletion at nucleotide position 813 (based on FIG. 9 numbering). Although this mutation (which occurred in cloning the synthetic p41d gene) resulted in a truncation in the p41d portion of the fusion protein, the protein produced was characterized for its diagnostic potential.

Production and Purification

Ten ml of LB/Amp in a 100 ml flask was inoculated with 100 ul of an overnight pTB310A/JM109 culture. After shaking at 37° C. for one and one-half hours, IPTG was added to the culture to a concentration of 1 mM, and the cells were grown for four more hours. An aliquot (1 ml) of the culture was pelleted and lysed in an appropriate volume of 1×treatment buffer to give a final concentration of cells of 10 0D$_{600}$ absorbance units. This sample, referred to as WCL (whole cell lysate), was used to measure the amount of fusion protein relative to total cellular proteins. The remaining 9 ml of cell culture was centrifuged (five minutes, 5000 rpm) and the cells were resuspended in 10 mM Tris (400 µl), pH 8.0, 1 mM EDTA with 2 mg/ml lysozyme. After fifteen minutes on ice, 10 ul of 20% Triton X-100 was added, and the cells were sonicated (6×30 sec). The lysate was spun in an Eppendorf centrifuge for five minutes. The supernatant was collected, and the pellet was resuspended in 8M urea (400 ul). The fusion protein present in the resuspended pellet fraction is about 75% pure based on Commassie stained gels.

Western and Immunoblots

Figure 10:
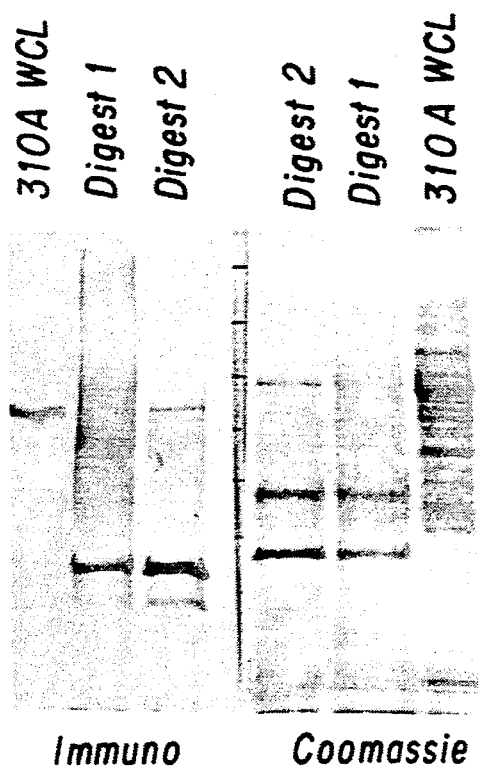
FIG. 10 illustrates the acid hydrolysate of the fusion protein expressed from pTB310. Coomassie brilliant blue-stained SDS-PAGE is pictured on the right. An immunoblot of an SDS-PAGE using human AIDS positive serum is shown on the left. Refer to text, Example 5B, for details.

A sample (10 ul) of pTB310A/JM109 WCL was loaded on a 0.7 mm thick 12.5% SDS-polyacrylamide gel, along with prestained protein molecular weight standards, WCL from JM109 without plasmid, and WCL from JM109 containing pTB210 (unfused CKS). Gel was run at 150 volts and terminated when bromophenol blue sample loading dye had reached the bottom of the gel. Proteins were then electrophoretically transferred to nitrocellulose. Immunoblotting was carried out as described in Example 3B. An example of pTB310A/JM109 WCL on a stained gel and immunoblot is shown in FIG. 10.

Chemical cleavage of fusion protein

An aliquot (30 ul) of the urea soluble fraction was diluted with ten volumes of water, and the insoluble fusion protein was pelleted by centrifugation. The protein was then dissolved in 30 ul of 6M guanidine hydrochloride, and 70 µl 98% formic acid added (Digestion 1). In a parallel experiment, 70 µl 98% formic acid was added to an aliquot (30 µl) of the urea fraction directly (Digestion 2). Following two days incubation at 42° C., ten volumes of water were added, and the insoluble proteins were pelleted by centrifugation. The pellet was resuspended in 1×treatment buffer (100 µl), and 10 µl was used per well on 12.5% SDS-polyacrylamide gel. FIG. 10 shows a sample of the cleaved products (Digestion 1 and Digestion 2) both on a Commassie-stained gel and an immunoblot (using HIV-1 positive human serum as primary antibody). Only two major bands are visible on the Commassie-stained gel. These represent the products of cleavage at the unique Asp-Pro bond: the CKS portion, MW=26.5 kDa and the p41 portion, MW=23.5 kDa. Peptide sequencing confirmed that the lower molecular weight band was indeed the p41 peptide, and that the amino terminal residue was proline which results from expected cleavage between the Asp and Pro.

C. Characterization of the pTB310B/JM109 clone

The clone containing the correct gene for the CKS-p41d fusion, pTB310B, was cultured and assayed for expression. The fusion protein represents 10–20% of the total cellular protein (dependent on growth and induction conditions).

D. Addition of the p12O carboxy terminal region

A synthetic DNA fragment which encoded the carboxy terminal 42 amino acids of HIV-1 p12O (Insert 1, FIG. 9) was inserted into the NarI site of pTB310A and pTB310B at nt 15. The resulting clones pTB319/JM109 and pTB321/JM109, respectively, expressed the triple fusion protein at levels of up to 20% total cellular protein.

EXAMPLE 6

Fusion protein—CKS/HSVII gG2

A 1.1 kb fragment containing the Herpes Simplex Virus II (HSVII) gG2 gene (encoding a major envelope glycoprotein) was isolated following digestion with AatII and XbaI. A synthetic linker was ligated to the XbaI end to generate an AatII end. Both ends were then made blunt by treating the 3' overhangs with T4 polymerase.

Figure 11:
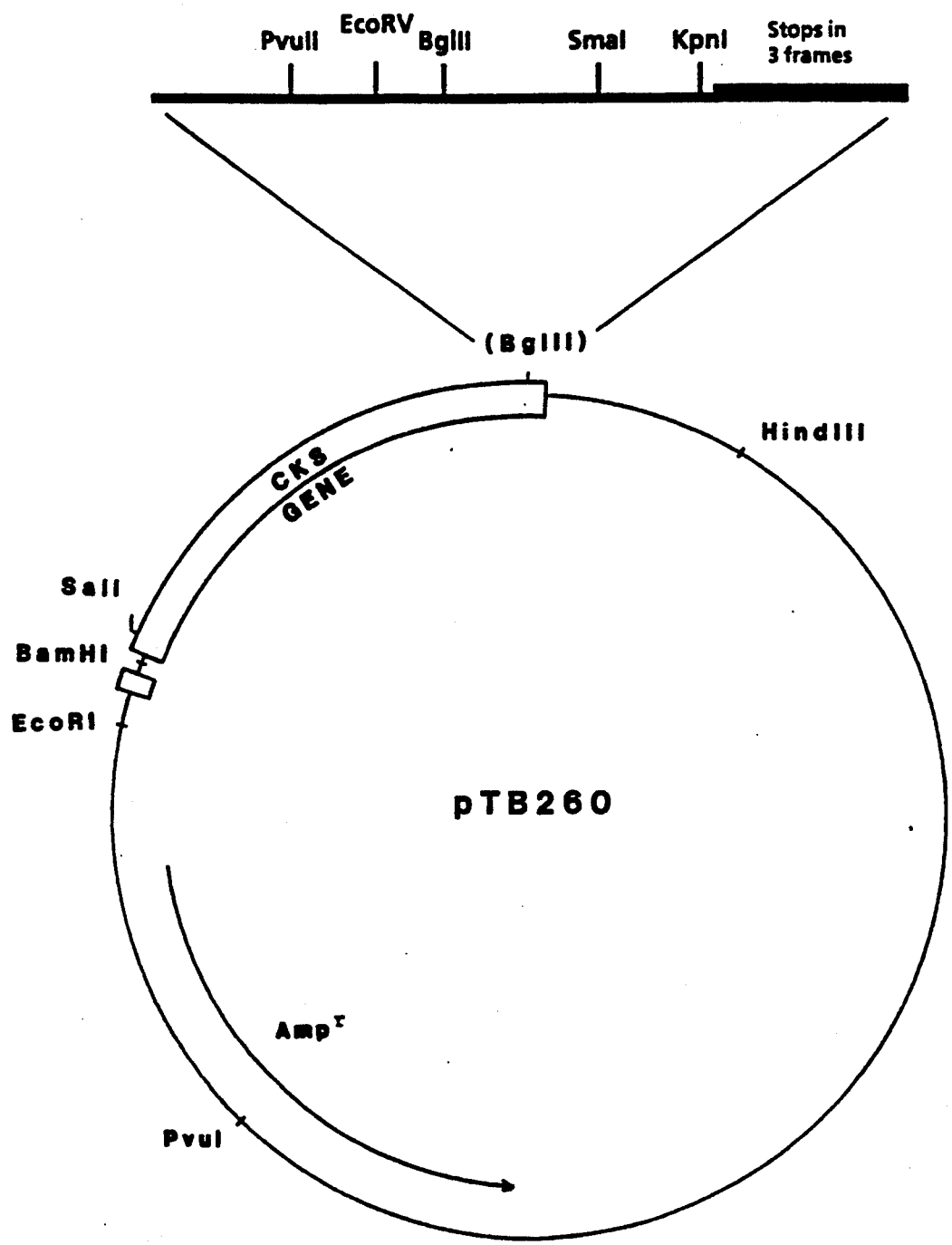
FIG. 11 is a graphic representation of a plasmid pTB260 used as a cloning vehicle in this invention.

The vector in this example was pTB260 (FIG. 11). It was constructed by ligating a synthetic fragment with multiple restriction sites into the BglII site of pTB201. In cloning the fragment, the original BqlII site from pTB201 was inactivated and thus, the BglII site in the linker 8 fragment is unique.

To facilitate cloning the blunt-ended DNA fragment containing the gG2 gene and to put the gene in the proper reading frame of kdsB, the BglII digested pTB260 was made blunt-ended by filling in the overhangs using Klenow and dNTP's. Following ligation of the gG2 DNA with pTB260, the DNA was used to transform competent TB-1 cells. Whole cell lysate from transformants run on gels and immunoblotted with rabbit serum against HSVII proteins gave a visible band of the proper molecular weight.

EXAMPLE 7

Fusion protein—CKS/Kringle region of tPA

Figure 12:
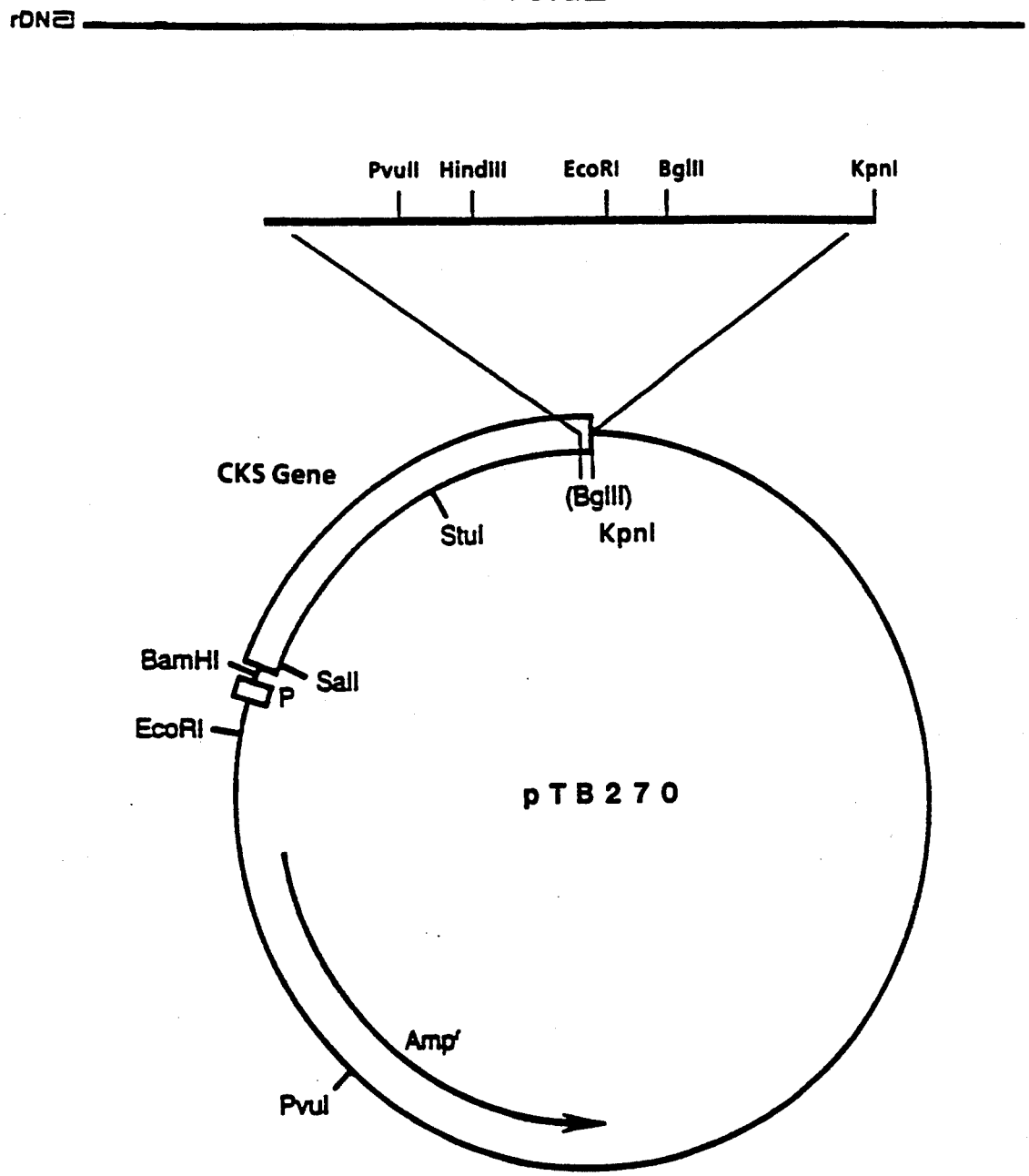
FIG. 12 is a graphic representation of a plasmid pTB270 used as a cloning vehicle in this invention.

A gene coding for the "kringle" (Patthy, L., *Cell* 41: 657 [1985]) region of tissue-plasminagenactivator was synthesized and cloned as a 335 bp HindIII-KpnI fragment into pTB270 (Zablen, L. B., unpublished). The pTB270 vector (FIG. 12) was a derivation of pTB210 which was constructed by ligating a synthetic multicloning site linker into BalII-KpnI digested pTB210. The pTB270 plasmid was then digested with HindIII-KpnI and ligated with the Kringle-region gene fragment. Transformation was carried in competent XL-1 Blue cells (Stratagene). Clones containing the proper insert were confirmed by DNA sequencing of the plasmids. The level of the fusion protein reached 30%–40% of the total cellular proteins.

The CKS/Kringle protein was extracted from a culture by lysing the cells as in Example 5B, precipitating the cellular debris, and collecting the supernatant which contained the soluble fusion protein. Further purification was accomplished by "salting out" the protein. Briefly, ammonium sulfate was added to 10% (w/v), and the insoluble proteins were pelleted by centrifugation. The pellet of this fraction, after assaying to demonstrate the absence of fusion protein, was discarded. Ammonium sulfate was added to the supernatant to a final concentration of 30%, and the insoluble proteins were pelleted. This pellet contained 70% of the starting fusion protein amount and was 75% pure.

EXAMPLE 8

Fusion protein—CKS/SPL(pVal)

A. A human lung surfactant gene, SPL(pVal) (patent application Ser. No. 101,680 (October 1987) filed by Whitsett et al.), contained within an 820 bp EcoRI fragment was cloned into pTB210. The overhanging EcoRI ends were filled using Klenow and dNTP's. The blunt-ended fragment was then ligated into PvuII digested pTB210. Following transformation into competent XL-1 Blue cells (Stratagene), DNA was isolated from a number of transformants and mapped with restriction endonucleases to identify clones with the insert in proper orientation. Expression level of the fusion protein based on whole cell lysates was 3%. The protein could be purified to about 50% purity by cell lysis and pelleting as described in Example 5B. The fusion protein was used to generate antibodies against the SPL peptide by immunizing rabbits with gel purified product.

Figure 13:
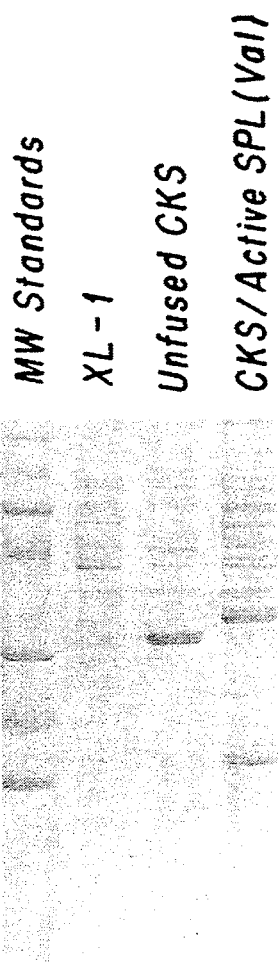
FIG. 13 is a coomassie brilliant blue-stained SDS-PAGE gel. Approximately equal numbers of cells of each clone type were lysed and loaded on the gel. The lane marked "XL-1" is the cell lysate from the XL-1 Blue strain with no plasmid. "Unfused CKS" is lysate from XL-1. Blue cells containing the pTB201 CKS-expressing vector. "CKS/Active SPL (val)" is lysate from an XL-1 cell line which contains the active region of the pval lung surfactant gene in fusion with the kdsB gene on the pTB201 plasmid.

B. A hydrid gene containing kdsB with the 139 nt active region of pVal was constructed by cloning a BglII-HindIII-ended synthetic fragment encoding the active region (refer to patent) into BqlII-HindIII digested pTB201. Assays of whole cell lysates indicated that expression levels of up to 40% of the total cellular protein were obtained (FIG. 13).

EXAMPLE 9

Fusion protein—CKS/SPL(phe)

A human lung surfactant gene, SPL(phe) (disclosed in the Whitsett patent application above), contained within a 1635 bp EcoRI-HindIII fragment was cloned into pTB210. The gene was originally isolated from a clone, Phe- 7-1, as a 1945 bp EcoRI fragment, blunt-end filled using Klenow and dNTP's, then digested with HindIII. This fragment was ligated into PvuII-HindIII digested pTB210 and transformed into competent XL-1 Blue cells. The CKS/SPL(phe) fusion protein level was 9% of the total cellular protein. The fusion protein was 50% pure in the pellet following lysis of the cells (procedure described in Example 5B). Gel purified CKS/SPL(Phe) was used to immunize rabbits to generate antibodies against the SPL(Phe) portion of the protein.

EXAMPLE 10

Fusion protein—CKS/synthetic HIV-2 TMP Fragment

In this example, a synthetic DNA fragment containing a portion of the HIV-2 (human immunodeficiency virus II) transmembrane protein (TMP) was cloned into the CKS expression vector. The resulting gene coded for a protein fusion consisting of CKS (less nine residues at the carboxy terminus), a ten amino acid residue linker, and the major epitope of the HIV-2 virus (envelope amino acid positions 502–609, numbering by Guyader, et al., *Nature* 326: 662, [1987]) followed by another ten amino acid residue linker. This fusion protein was expressed to a level of up to 15% of the total cellular protein and proved useful in the detection of sera containing HIV-2 antibodies.

A. Synthesis and cloning of the HIV-2 TMP fragment

Figure 15:
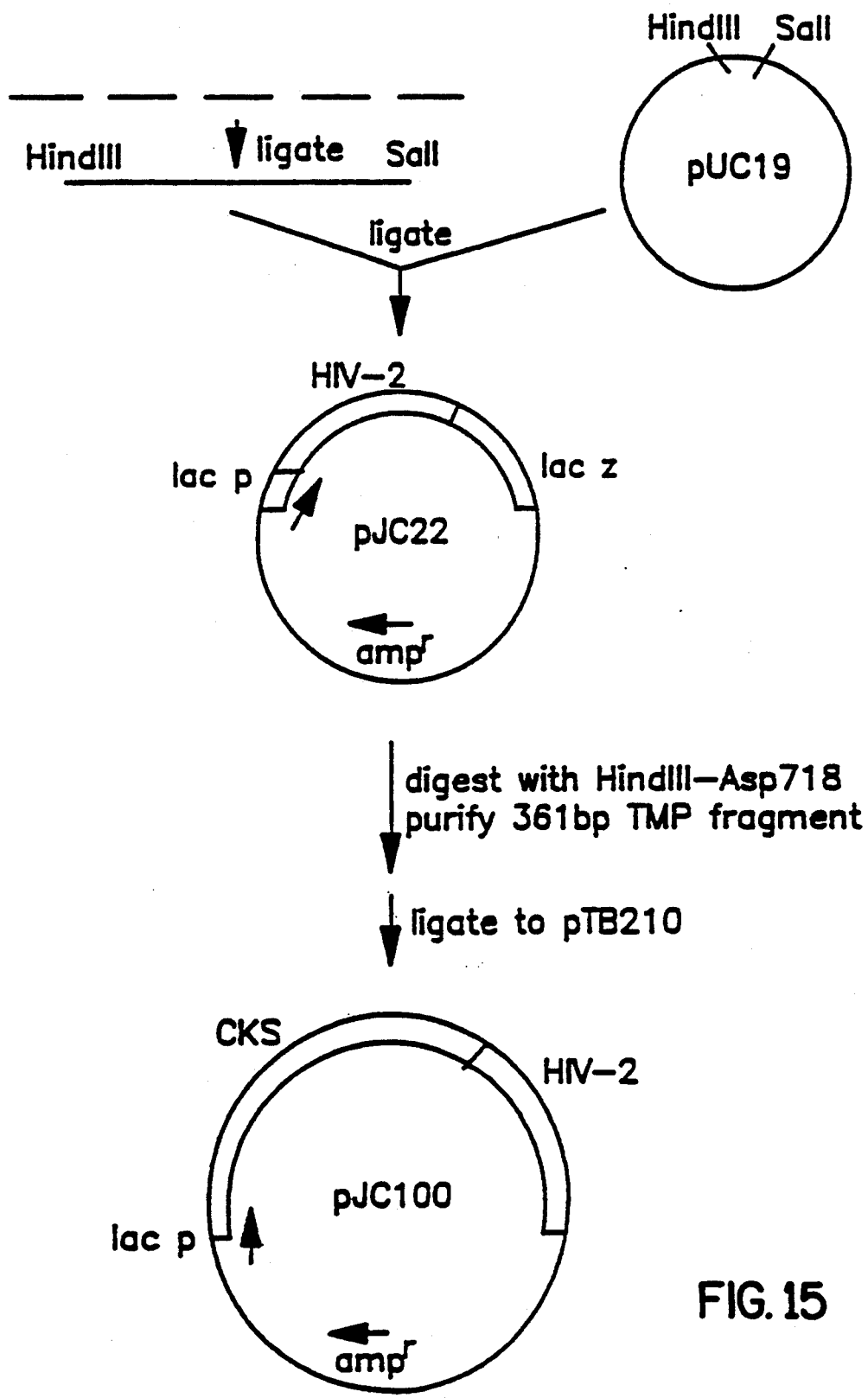
FIG. 15 is a schematic representation of the construction of pJC22 and pJC100.

The HIV-2 TMP fragment codes for the amino terminal 108 amino acids of the HIV-2 TMP (from Tyr 502 to Trp 609) identified in FIG. 14. The gene fragment was synthesized using the method of oligonucleotide directed double-stranded break repair disclosed in U.S. patent application Ser. No. 883,242 filed Jul. 8, 1986 by Mandecki which is incorporated herein by reference. The five DNA fragments comprising the TMP gene fragment were ligated together and cloned at the HindIII-SalI sites of pUC19 (FIG. 15). A clone, designated pJC22, was identified by restriction mapping and its primary nucleotide sequence confirmed. The clone pJC22 was digested with HindIII-Asp718 to release a 361 bp fragment containing the synthetic HIV-2 TMP gene fragment which was ligated into the HindIII-Asp718 sites of plasmid pTB210 and transformed into XL1 cells. A clone, designated pJC100, was isolated and restriction mapped to identify the hybrid gene of kdsb and HIV-2 TMP.

B. Characterization of fusion protein encoded by pJC100

Fifty (50) ml of LB/Amp in a 250 ml flask was inoculated with 500 µl of an overnight culture of either pTB210/XL1 or pJC100/XL1 and allowed to shake at 37° C. until the $OD_{600}$ reached 0.5 absorbance units (1.5–2.0 hours) at which time IPTG was added to a final concentration of 1 mM. An aliquot (1.5 ml) of the culture was removed every hour for four hours, and then a final aliquot taken at 18 hours post induction. These aliquots were pelleted and lysed in an appropriate volume of 1× treatment buffer to give a final concentration of cells of 10 OD$_{600}$ absorbance units. Aliquots of each timepoint (15 μl) were electrophoresed on 12.5% SDS/PAGE gels and transferred electropohoretically to nitrocellulose. Immunoblotting was carried out as described in Example 3B using HIV-2 positive human sera or goat antibody directed against CKS. The HIV-2 positive human sera demonstrated no signal to the pTB210/XL1 culture and a strong signal to the pJC100/XL1 culture at the expected molecular weight. The goat antibody against CKS reacted strongly with both cultures at the expected molecular weights. A similar SDS/PA.GE gel was run and Coomassie blue staining demonstrated that expression of the fusion protein peaked at: 3–4 hours post induction at a level of 15% of total protein.

Figure 16:
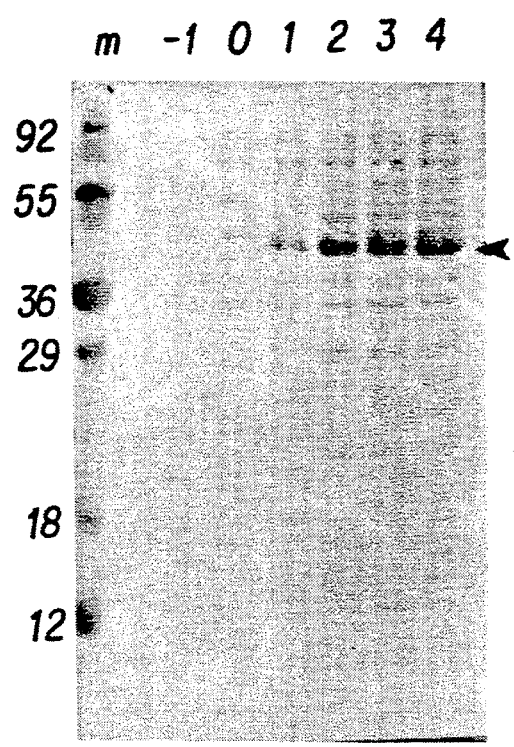
FIG. 16 is a coomassie brilliant blue stained gel of clone pJC100 induced for the specified time in hours. M is protein molecular weight markers.

FIG. 16 demonstrates the expression of the CKS/HIV-2 TMP fusion protein in a ten liter fermenter as seen by Coomassie blue staining of a 12.5% SDS/PAGE gel of various time points before and after induction. A partial purification of the fusion protein was obtained by the method described in Example 5B with similar results.

EXAMPLE 11

Use of CKS Fusion Protein in a Screening Assay

Media such as Luria-Bertani (LB) and Superbroth II (Dri Form) were obtained from Gibco Laboratories Life Technologies, Inc., Madison, Wis. Restriction enzymes, Klenow fragment of DNA polymerase I, T4 DNA ligase, T4 polynucleotide kinase, nucleic acid molecular weight standards, M13 sequencing system, X-gal (5-bromo-4-chloro-3-indonyl-B-D-galactoside), IPTG, glycerol, Dithiothreitol, 4-chloro-1-napthol were purchased from Boeringer Mannhein Biochemicals, Indianapolis, Ind.; or New England Biolabs, Inc., Beverly, Mass.; or Bethesda Research Laboratories Life Technologies, Inc., Gaithersburg, Md. Prestrained protein molecular weight standards, acrylamide (crystallized, electrophoretic grade 99%); N-N' Methylene-bis-acrylamide (BIS); N,N,N',N',-Tetramethylethylenediamine (TEMED) and sodium dodecylsyulfate (SDS) were purchased from BioRad Laboratories, Richmond, Calif. Lysozome and ampicillin were obtained from Sigma Chemical Co., St. Louis, Mo. Horseradish peroxidase (HRPO) labeled secondary antibodies were obtained from Kirkegaard & Perry Laboratories, Inc., Gaithersburg, Md. Seaplaque ® agarose (low melting agarose) was purchased from FMC Bioproducts, Rockland, Me.

T50E10 contained 50 mM Tris, pH 8.0, 10 mM EDTA; 1× TG contained 100 mM Tris, pH 7.5 and 10% glycerol; 2× SDS/PAGE loading buffer consisted of 15% glycerol, 5% SDS, 100 mM Tris base, 1M B-mercaptoethanol, and 0.8% Bromophenol blue dye; TBS contained 50 mM Tris, pH 8.0, and 150 mM sodium chloride; blocking solution consisted of 5% Carnation nonfat dry milk in TBS.

Host Cells Cultures, DNA Sources and Vectors

*E. coli* JM103 cells, pUC8, pUC18, pUC19 and M13 cloning vectors were purchased from Pharmacia LKB Biotechnology, Inc., Piscataway, N.J.; Competent Epicurean ™ coli stains XL-1Blue and JM109 were purchased from Strategene Cloning Systems, LaJolla, Calif. RR1 cells were obtained from Coli Genetic Stock Center, Yale University, New Haven, Conn.; and *E. coli* CAG456 cells were from Dr. Carol Gross, University of Wisconsin, Madison, Wis. Vector pRK248.clts was obtained from Dr. Donald R. Helinski, University of California, San Diego, Calif.

General Methods

All restriction enzyme digestions were performed according to suppliers' instructions. At least 5 units of enzyme were used per microgram of DNA, and sufficient incubation was allowed to complete digestion of DNA. Standard procedures were used for minicell lysate DNA preparation, phenol-chloroform extraction, ethanol precipitation of DNA, restriction analysis of DNA on agarose, and low melting agarose gel purification of DNA fragments (Maniatis et al., *Molecular Cloning. A Laboratory Manual*, New York: Cold Spring Harbor [1982]). Plasmid isolations from *E. coli* strains used the alkali lysis procedure and cesium chloride-ethidium bromide density gradient method (Maniatis et al., supra). Standard buffers were used for T4 DNA ligase and T4 polynucleotide kinase (Maniatis et al., supra).

A. Preparation of CKS-CORE

1. Construction of the Plasmid pJO200. The cloning vector pJO200 allowed the fusion of recombinant proteins to the CKS protein. The plasmid consists of the plasmid pBR322 with a modified lac promoter fusion to a KdsB gene fragment (encoding the first 239 amino acids of the entire 248 amino acids of the *E. coli* CMP-KDO synthetase of CKS protein), and a synthetic linker fused to the end of the KdsB gene fragment. The cloning vector pJO200 is a modification of vector pTB201. The synthetic linker includes: multiple restriction sites for insertion of genes; translational stop signals, and the trpA rho-independent transcriptional terminator.

2. Preparation of HCV CKS-Core Expression Vector. Six individual nucleotides representing amino acids 1–150 of the HCV genome were ligated together and cloned as a 466 base pair EcoR1-BamHI fragment into the CKS fusion vector pJO200. The complete DNA sequence of this plasmid, designated pHCV-34, and the entire amino acid sequence of the pHCV recombinant antigen produced is as described in U.S. patent application Ser. No. 07/614,069, filed Nov. 7, 1990 and U.S. patent application Ser. No. 07/572,822 filed Aug. 24, 1990, which have been published as EPO Publication No. 0 472 207 A2, enjoy common ownership and are incorporated herein by reference. The resultant fusion protein HCV CKS-CORE (HCV-34), consisted of 239 amino acids of CKS, seven amino acids contributed by linker DNA sequences, and the first 150 amino acids of HCV.

The pHCV-34 plasmid and the CKS plasmid pTB210 were transformed into *E. coli* K-12 strain XL-1 (recAi, endA1, gyrA96, thi-1, hsdR17, supE44, relA1, lac/F', proAB, LaclqZDM15, TN10) cells made competent by the calcium chloride method. In these constructions the expression of the CKS fusion proteins was under the control of the lac promoter and was induced by the addition of IPTG. These plasmids replicated s independent elements, were nonmobilizable and were maintained at approximately 10–30 copies per cell.

3. Characterization of Recombinant HCV-CORE. In order to establish that clone pHCV-34 expressed the unique HCV-34 protein, the pHCV-34/XL-1 culture was grown overnight at 37° C. in growth media consisting of yeast extract, trytone, phosphate salts, glucose, and ampicillin. When the culture reached OD of 1.0, IPTG was added to a final concentration of 1 mM to induce expression. Samples were removed at i hour intervals, and cells were pelleted and resuspended to an OD600 of 1.0 in 2×SDS/PAGE loading buffer. Aliquots (15 μl) of the prepared samples were separated on duplicate 12.5% SDS/PAGE gels.

One gel was fixed in a solution of 50% methanol and 10% acetic acid for 20 minutes at room temperature, and then stained with 0.25% Coomassie blue dye in a solution of 50% methanol and 10% acetic acid for 30 minutes. Destaining was carried out using a solution of 10% methanol and 7% acetic acid for 3 to 4 hours, or until a clear background was obtained. Results showed that the recombinant protein HCV-34 had an apparent mobility corresponding to a molecular size of 48,000 daltons. This compared acceptably with the predicted molecular mass of 43,750 daltons.

Proteins from the second 12.5% SDS/PAGE gel were electrophoretically transferred to nitrocellulose for immunoblotting. The nitrocellulose sheet containing the transferred proteins was incubated with blocking solution for one hour and incubated overnight at 4° C. with HCV patients' sera diluted in TBS containing *E. coli* K-12 strain XL-1 lysate. The nitrocellulose sheet was washed three times in TBS, then incubated with HRPO-labeled goat anti-human IgG (previously diluted in PBS containing 10% fetal calf sera). The nitrocellulose was washed three times with TBS and the color was developed in TBS containing 2 mg/ml 4-chloro-1-napthol, 0.02% hydrogen peroxide and 17% methanol. Clone pHCV-34 demonstrated a strong immunoreactive band at 48,000 daltons with the HCV patients' sera. Thus, the major protein in the Coomassie stained protein gel was immunoreactive. Normal human serum did not react with any component of HCV-34.

B. Preparation of HCV CKS-33C-BCD Expression Vector

The construction of this recombinant clone expressing the HCV CKS-33-BCD recombinant protein (HCV-31) was carried out in three steps described below. First, a clone expressing the HCV CKS-BCD recombinant protein (HCV-23) was constructed, designated pHCV-23. Second, a clone expressing the HCV CKS-33 recombinant protein (HCV-29) was constructed, designated pHCV-29. Lastly, the HCV BCD region was excised from pHCV-23 and inserted into pHCV-29 to construct a clone expressing the HCV CKS-33-BCD recombinant protein (HCV-31), designated pHCV-31.

To construct the plasmid pHCV-23, thirteen individual oligonucleotides representing amino acids 1676–1931 of the HCV genome were ligated together and cloned as three separate EcoR1-BamH1 subfragments into the CKS fusion vector pJO200. After subsequent DNA sequence confirmation, the three subfragments, designated B, C, and D respectively, were digested with the appropriate restriction enzymes, gel purified, ligated together, and cloned as a 781 base pair EcoR1-BamH1 fragment in the CKS fusion vector pJO200. The resulting plasmid, designated pHCV-23, expressed the HCV CKS-BCD recombinant protein (HC-23) under control of the lac promoter. The HCV CKS-BCD recombinant protein (HCV-23) consisted of 239 amino acids of CKS, seven amino acids contributed by linker DNA sequences, 256 amino acids from the HCV NS4 region (amino acids 1676–1931) and 10 additional amino acids contributed by linker DNA sequences.

To construct the plasmid pHCV-29, twelve individual oligonucleotides representing amino acids 1192–1457 of the HCV genome were ligated together and cloned as two separate EcoR1-BamH1 subfragments in the CKS fusion vector pJO200. After subsequent DNA sequence confirmation, the two subfragments were digested with the appropriate restriction enzymes, gel purified, ligated together and cloned again as an 816 base pair EcoR1-BamH1 fragment in the CKS fusion vector pJO200. The resulting plasmid, designated as pHCV-29, expressed the CKS-33 recombinant protein (HCV-29) under control of the lac promoter. The HCV CKS-33 recombinant protein (HCV-29) consisted of 239 amino acids of CKS, eight amino acids contributed by linker DNA sequences, and 266 amino acids from the HCV NS3 region (amino acids 1192–1457).

To construct the plasmid pHCV-31, the 781 base pair EcoR1-BamH1 fragment from pHCV-23 representing the HCV-BCD region was linker-adapted to produce a Cla1-BamH1 fragment which then was gel purified and ligated into pHCV-29 at the Cla1-BamH1 sites. The resulting plasmid, designated as pHCV-31, expressed the HCV-31 recombinant protein under control of the lac promoter. The HCV CKS-33-BCD recombinant protein (HCV-31) consisted of 239 amino acids of CKS, eight amino acids contributed by linker DNA sequences, 266 amino acids of the HCV NS3 region (amino acids 1192–1457), 2 amino acids contributed by linker DNA sequences, 256 amino acids of the HCV NS4 region (amino acids 1676–1931), and 10 additional amino acids contributed by linker DNA sequences. The pHCV-31 plasmid was transformed into *E. coli* K-12 strain XL-1 in a manner similar to the pHCV-34 and CKS-pTB210 plasmids, previously described in this example.

1. Characterization of Recombinant HCV CKS-33-BCD

Characterization of recombinant protein HCV CKS-33-BCD was carried out in a manner similar to that previously described for HCV CKS-Core. SDS/PAGE gels were run for *E. coli* lysates containing the plasmids pHCV-29, pHCV-23 and pHCV-31 expressing the recombinant fusion proteins CKS-33c (HCV-29), CKS-BCD (HCV-23) and CKS-33-BCD (HCV 31), respectively. Molecular weight standards also were run on these gels. The results showed (a) that the recombinant HCV-29 fusion protein had an apparent mobility corresponding to a molecular size of 60,000 daltons, which compared acceptably to the predicted molecular mass of 54,911; (b) that the recombinant HCV-23 fusion protein had an apparent mobility corresponding the a molecular size of 55,000 daltons, which compared acceptably to the predicted molecular mass of 55,000 daltons; and (c) that the recombinant HCV-31 fusion protein had an apparent mobility corresponding to a molecular size of 90,000 daltons, which compared acceptably to the predicted molecular weight of 82,995 daltons. Further, an immunoblot was run on one of the SDS/PAGE gels derived from the pHCV-31/X1-1 culture. Human sera from an HCV exposed individual reacted strongly with the major HCV-31 band at 90,000 daltons. Normal human serum did not react with any component of the HCV-31 (CKS-33-BCD) preparations.

C. Screening Assay

Polystyrene beads first were washed with distilled water and propanol, and then incubated with a solution containing recombinant [HCV-31 diluted to 0.5 to 2.0 μg/ml and HCV-34 diluted to 0.1 to 0.5 μg/ml in 0.1M NaH$_2$PO$_4$•H$_2$O with 0.4M NaCl and 0.0022% Triton X-100, pH 6.5.] The beads were incubated in the antigen solution for 2 hours (±10 minutes) at 38°–42° C., washed in phosphate buffered saline (PBS) soaked in 0.1% (w/v) Triton X-100 in PBS for 60 minutes at 38°–42° C. The beads then were washed two times in PBS, overcoated with a solution of 5.0% (w/v) bovine serum albumin (BSA) in PBS for 60 minutes at 38°–42° C., and washed one time in PBS. Finally, the beads were overcoated with 5% (w/v) sucrose in PBS, and dried under nitrogen or air.

The polystyrene beads coated with HCV-31 and HCV-34 were used in an antibody capture format. Ten (10) μl of sample were added to the wells of a reaction tray along with 400 μl of s sample diluent and the recombinant protein-coated bead. The sample diluent consisted of 10% (v/v) bovine serum and 20% (v/v) goat serum in 20 mM Tris phosphate buffer containing 0.15% (v/v) Triton X-100, 1% (w/v) BSA, 1% $E.$ $coli$ lysate and 500 μg/ml or less CKS lysate. After one hour of incubation at 40° C., the beads were washed and 200 μl of indicator reagent was added to the wells of the reaction tray. The preferred indicator reagent (conjugate) is goat anti-human IgG horseradish peroxidase conjugate. After one hour of incubation with the conjugate at 40° C., the beads were washed, exposed to the OPD substrate for 30 minutes at room temperature, and the reaction stopped by adding 1N H$_2$SO$_4$. The absorbance was read at 492 nm.

It was determined that in order to maintain acceptable specificity, the cutoff for the assay should be at least 5 to 7 standard deviations above the absorbance value of the normal population mean. In addition, it generally has been observed that acceptable specificity is obtained when the population mean runs at a sample to cutoff (S/CO) value of 0.25 or less. Consistent with these criteria, a "preclinical" cutoff for the screening assay was selected which clearly separated most of the presumed "true negative" from the "true positive" samples. The cutoff value was calculated as the sum of the positive control mean absorbance value multiplied by 0.25 and the negative control mean absorbance value. The cutoff may be expressed algebraically as:

Cutoff value = $0.25 PCx + NCx$.

Testing may be performed manually or by various degrees of automation. An example of an automated system is the Abbott Commander ® system, which employs a pipetting device referred to as the Sample Management Center (SMC) and a wash/dispense/read device referred to as the Parallel Processing Center (PPC). The optical reader used in the PPC has dual wavelength capabilities that can measure differential absorbancies (peak band and side band) from the sample wells. These readings are converted into results by the processors' control center.

Concentrated conjugate was previously titered to determine working concentration. A 20-fold concentrate of the working conjugate solution then was prepared by diluting the concentration in diluent. The 20× concentrate was sterile filtered and stored in plastic bottles till used.

The conjugate diluent included 10% (v/v) bovine serum, 10% (v/v) goat serum and 0.15% Triton X-100 in 20 mM Tris buffer, pH 7.5 with 0.01% gentamicin sulfate, 0.01% thimersol and red dye. The conjugate was sterile filtered and filled in plastic bottles.

Positive controls were prepared from plasma units positive for antibodies to HCV, including plasma with antibodies reactive to HCV-31 and HCV-34. The units were recalcified and heat inactivated at 59°–61° C. for 12 hours with constant stirring. The pool then was aliquoted and stored at −20° C. or at 2°–8° C. in 0.1% sodium azide. Likewise, negative controls were prepared from recalcified human plasma negative for antibodies to HCV-31 and HCV-34 proteins of HCV. The plasma also was negative for antibodies to human immunodeficiency virus (HIV) and hepatitis B surface antigen (HBsAg). These units also were pooled, had 0.1% sodium azide as a preservative, and were sterile filtered, aliquoted and stored until use.

D. Screening Assay Performance

Seven chimpanzees were tested pre-inoculation with HCV and following inoculation by using the screening assays described herein which employed an HCV c100-3 polypeptide attached to a solid phase, or the screening assay described herein which employed CKS recombinant proteins HCV-31 and HCV-34. Both assays gave negative results before inoculation and both assays detected the presence of antibodies after the animal had been infected with HCV. However, in the comparison of the two assays, the assay utilizing HCV-31 and HCV-34 detected seroconverions to HCV antigens at an earlier or equivalent bleed date in six of the seven chimpanzees. Data from these chimpanzee studies clearly demonstrate that detection of HCV antibodies can be accomplished utilizing the CKS proteins of the invention, and that detection of HCV antibodies is greatly increased with the assay utilizing the HCV-31 and HCV-34 proteins.

EXAMPLE 12

Competition Assay

To perform the assay, a recombinant polypeptide representing epitopes within the c100-3 region of HCV such as CKS-BCD (HCV-23) was solubilized and mixed with a sample diluent to a final concentration of 0.5 to 50 μg/ml. Ten (10) μl of test sample or diluted test sample is added to a reaction well followed by 400 μl of the sample diluent containing the CKS recombinant protein and optionally, may be preincubated for about 15 minutes to two hours. A bead coated with c100-3 antigen then is added to the reaction well and incubated for one hour at 40° C. After washing, 200 μl of a peroxidase labelled goat anti-human IgG in conjugate diluent (the indicator reagent) is added and the reaction is incubated for one hour at 40° C. After washing, OPD substrate is added and the reaction is incubated at room temperature for 30 minutes. The reaction is terminated by the addition of 1N sulfuric acid, and the absorbance of the signal generated is read at 492 nm.

Samples which contain antibodies to c100-3 antigen generate a reduced signal caused by the competitive binding of the fusion proteins to these antibodies in solution. The percentage of competitive binding may be calculated by comparing the absorbance value of the sample in the presence of a recombinant polypeptide to the absorbance value of the sample assayed in the absence of a recombinant polypeptide at the same dilution.

EXAMPLE 13

Immunodot Assay

The immunodot assay system uses a panel of purified CKS recombinant proteins placed in an array on a nitrocellulose solid support. The prepared solid support is contacted with a test sample and captures specific antibodies to HCV antigens. The captures antibodies are detected by a conjugate-specific (indicator reagent specific) reaction. Preferably, the conjugate specific reaction is quantified using a reflectance optics assembly within an instrument which has been described in U.S. patent application Ser. No. 07/227,408, and related applications and patents, discussed supra. Briefly, a nitrocellulose-base test cartridge is treated with multiple antigenic CKS recombinant polypeptides. Each CKS recombinant polypeptide is contained within a specific reaction zone on the test cartridge. After all the antigenic CKS recombinant polypeptides have been placed on the nitrocellulose, excess binding sites on the nitrocellulose are blocked. The test cartridge then is contacted with a sample such that each antigenic recombinant polypeptide in each reaction zone will react if the sample contains the appropriate antibody. After reaction, the test cartridge is washed and any antigen-antibody reactions are identified using suitable well-known reagents.

In a preferred immunodot assay, the CKS recombinant polypeptides HCV-23, HCV-29, HCV-34, and c100-3 were diluted in the preferred buffers, pH conditions, and spotting concentrations as described in Table 1, and applied to a preassembled nitrocellulose test cartridge. After drying the cartridge over night at room temperature, the non-specific binding capacity of the nitrocellulose phase was blocked. The blocking solution contained 1% porcine gelatin, 1% casein enzymatic hydrolysate, 5% Tween-10, 0.1% sodium azide, 0.5M sodium chloride and 20 mM Tris, pH 7.5

TABLE 1

| Plasmid/Protein | ng/Spot | Spotting Buffer |
| --- | --- | --- |
| c100 | 100–150 | 20 mM Tris-HCl, 0.9% NaCl, 0.015% SDS, pH 8.3 |
| pHCV-23/ CKS-BCD | 100–150 | 20 mM Tris-HCl, 0.9% NaCl, 0.015% SDS, pH 8.3 |
| pHCV-29/ CKS-33c | 100–150 | 50 mM NaPhosphate, 0.01% Triton X-100, pH 6.5 |
| pHCV-34/ CKS-CORE | 75–100 | 50 mM NaPhosphate, 0.0025% Tween-20, pH 12.0 |

Forty (40) normal donors were assayed by following the method described above. The mean reflectance density value then was determined for each of the recombinant proteins. A cutoff value was calculated as the negative mean plus six standard deviations. Test cartridges were incubated with samples Nos. A00642 and 423. Test sample A00642 was from a convalescent non-A, non-B hepatitis patient, and had been diluted in negative human plasma from 1:100 to 1:12800. The other sample, 423, was from a paid plasma donor which had tested positive in an assay using a recombinant c100-3 polypeptide, diluted in negative human plasma from 1:40 to 1:2560. After sample incubation, sequential incubations with indicator reagents (a biotin-conjugated goat anti-human immunoglobulin-specific antibody, an alkaline phosphatase-conjugated rabbit anti-biotin specific antibody, and 5-bromo-4-chloro-3-indolyl phosphate) produced a colored product at the site of reaction. Sample to cutoff values (S/CO) were determined for all CKS HCV recombinant proteins. Those S/CO values greater than or equal to 1.0 were considered reactive. The limiting dilution was defined as the lowest dilution at which the S/CO was greater than or equal to 1.0. Each sample tested positive for all HCV CKS recombinant proteins.

It will be apparent to those of ordinary skill in the art that many modifications and variations of the present invention are possible without departing from the spirit and scope hereof, and that, accordingly, such limitations are imposed only as indicated by the appended claims.

What is claimed is:

1. In an assay for detecting anti-analyte antibody in a test sample wherein (a) at least one recombinant analyte-specific fusion protein is attached to a solid phase as a capture reagent and is contacted with the test sample for a time and under conditions suitable for fusion protein/antibody complexes to occur, and (b) an indicator reagent comprising a signal generating compound and a specific binding member for the analyte is contacted with said complexes for time sufficient for a reaction to occur, wherein the signal generated is an indication of the presence of the anti-analyte antibody in the test sample, and wherein the improvement comprises attaching a recombinant CKS fusion protein to the solid phase as the capture reagent.

2. The assay of claim 1 wherein the anti-analyte antibody is selected from the group consisting of anti-HCV antibody, anti-HIV-1 antibody, anti-HIV-2 antibody, anti-HTLV-I antibody and anti-HTLV-II antibody.

3. In a competitive assay for detecting the presence of an anti-analyte antibody specifically reactive with a protein in a fluid test sample wherein (a) first and second aliquots of the test sample are obtained, (b) the first aliquot of said sample is contacted with a recombinant fusion protein which is specific for said anti-analyte antibody and is attached to a solid support and (c) wherein the second aliquot is contacted with unattached recombinant fusion protein specific for said anti-analyte antibody and then contacted with said bound protein, wherein the improvement comprises a recombinant CKS-fusion protein specific for said anti-analyte antibody attached to the solid phase of step (b) and unattached recombinant CKS-fusion protein specific for said anti-analyte antibody in step (c).

4. The competitive assay of claim 3, wherein step (b) is incubated for about 15 minutes to 2 hours before performing step (c).

5. The competitive assay of claim 2 wherein step (b) and step (c) are performed simultaneously.

6. A test kit for use in detecting the presence of anti-analyte antibody in a test sample which test kit contains a container containing at least one protein specific for said anti-analyte antibody, and wherein the improvement comprises a container containing a CKS-fusion protein specific for said anti-analyte antibody.

7. The test kit of claim 6 wherein said CKS fusion protein is a CKS-HCV fusion protein.

8. The test kit of claim 6 wherein said CKS fusion protein is a CKS-HIV-1 fusion protein and/or a CKS-HIV-2 fusion protein.

9. The test kit of claim 6 wherein the CKS fusion protein is a CKS-HTLV-I fusion protein and/or a CKS-HTLV-II fusion protein.

10. The test kit of claim 6 wherein said CKS fusion protein is attached to a solid phase.

* * * * *